US007994389B2

(12) United States Patent     (10) Patent No.:   US 7,994,389 B2
Hill et al.     (45) Date of Patent:   Aug. 9, 2011

(54) **SOYBEAN GENES FOR RESISTANCE TO *APHIS GLYCINES***

(75) Inventors: Curtis B. Hill, Champaign, IL (US); Glen L. Hartman, Urbana, IL (US); Yan Li, Chicago, IL (US); Brian Diers, Urbana, IL (US); Shawn Carlson, Bondville, IL (US)

(73) Assignees: The Board of Trustees of the University of Illinois, Urbana, IL (US); The United States of America as represented by the Secretary of Agriculture, Washington, DC (US)

( * ) Notice: Subject to any disclaimer, the term of this patent is extended or adjusted under 35 U.S.C. 154(b) by 731 days.

(21) Appl. No.: 11/158,307

(22) Filed: Jun. 21, 2005

(65) Prior Publication Data

US 2006/0015964 A1   Jan. 19, 2006

Related U.S. Application Data

(60) Provisional application No. 60/581,501, filed on Jun. 21, 2004.

(51) Int. Cl.
*A01H 1/04* (2006.01)
*A01H 1/00* (2006.01)
(52) U.S. Cl. ......... 800/267; 800/265; 800/266; 800/260
(58) Field of Classification Search .................. 800/265, 800/266, 267, 312
See application file for complete search history.

(56) References Cited

U.S. PATENT DOCUMENTS

| | | | |
|---|---|---|---|
| 5,491,081 A | 2/1996 | Webb | |
| 5,689,035 A | 11/1997 | Webb | |
| 5,948,953 A | 9/1999 | Webb | |
| 6,054,300 A | 4/2000 | McKendree | |
| 6,162,967 A | 12/2000 | Webb | |
| 6,538,175 B1 | 3/2003 | Webb | |
| 2004/0034890 A1 | 2/2004 | St. Martin et al. | |

OTHER PUBLICATIONS

Narvel et al. 2001. Crop Sci 41: 1931-1939.*
Hill et al. 2004. Crop Sci 44: 98-106.*
Narvel et al. Crop Sci 41: 1931-1939, 2001.*
Rongwen et al. Theor Appl Genet 90: 43-48, 1995.*
Bissonnette, S. (2002) "Good News on Aphids: First Resistance Found," *Champaign-Urbana News Gazette* Aug. 4.
Zhu et al. (2006), "Fine Mapping of a Major Insect Resistance QTL in Soybean and its Interaction with Minor Resistance QTLs," *Crop Sci.* 46:1094-1099.
Auclair, J.L. (1989) "Host Plant Resistance," In; *Aphids: Their Biology, Natural Enemies, and Control*, vol. C., Harrewijn et al. ed., Elsevier, New York, pp. 225-265.
Bell-Johnson et al. (1998) "Biotechnology Approaches to Improving Resistance to SCN and SDS: Method for High Throughput Marker Assisted Selection," *Soybean Genet. Newlett.* 25:115-117.

Clark et al. (2002) "Transmissibility of Field Isolates of Soybean Viruses by *Aphis glycines,*" *Plant Dis.* 86:1219-1222.
Cregan et al. (1999) "An Integrated Genetic Linkage Map of the Soybean Genome," *Crop Sci.* 39:1464-1490.
Du Toit, F. (1987) "Resistance in Wheat (*Triricum aestivum*) to *Diuraphis noxia* (Homoptera: Aphididae)," *Cereal Res. Commun.* 15:175-179.
Harrewijn et al. (1989) "Integrated Aphid Management: General Aspects," In; *Aphids: Their Biology, Natural Enemies, and Control*, vol. C., Harrewijn et al. ed., Elsevier, New York, pp. 267-272.
Hartman et al. (2001) "Occurrence and Distribution of *Aphis Glycines* on Soybeans in Illinois in 2000 and its Potential Control," http://www.plantmanagementnetwork.org/php/default.asp.
Hill et al. (2002) "Resistance to the Soybean Aphid in Soybean and Other Legumes," *APS Annual Meeting*, Jul. 27-31, abstract.
Hill et al. (2004) "Resistance to the Soybean Aphid in Soybean Germplasm," *Crop Sci.* 44:98-106.
Hill et al. (2004) "Resistance of Glycine Species and Various Cultivated Legumes to the Soybean Aphid (Homoptera: Aphididae)," *J. Econ. Entomol.* 97(3)1071-1077.
Hill et al. (1996) "First Report of Transmission of *Soybean Mosaic Virus* and *Alfalfa Mosaic Virus* by *Aphis glycines* in the New World," *Plant Dis.* 85:561.
Hill et al. (2002) "Resistance to the Soybean Aphid in Soybean and Other Legumes," *Phytopathol.* 92:S36.
Hill et al. (2002) "Resistance to the Soybean Aphid in Soybean and Other Legumes," Poster, National Meeting of the American Phytopathological Society, Milwaukee, Wisconsin.
Hill et al. (Nov. 2002) Oral Research Report, North Central Soybean Virus Workers Conference, Iowa State University, Ames, IA.
Hill et al. (2003) "Resistance to the Soybean Aphid (*Aphis glycines*) has Been Discovered in Ancestral Soybean Germplasm," http://www.soydiseases.uiuc.edu/projects.php?id=1.
Hill et al. (2004) "Resistance to the Soybean Aphid in Soybean Germplasm and other Legumes," Abstract and poster, World Sobean Research Conference, Iguaça Fallls, Brazil.
Hirano et al. (1996) "Effects of Temperature on Development, Longevity and Reproduction of the Soybean Aphid, *Aphis glycines* (Homoptera: Aphididae)," *Appl. Entomol. Zool.* 31(1):178-180.
Hymowitz, T. (1970) "On the Domestication of the Soybean," *Econ. Bot.* 24:408-421.
Iwaki et al. (1980) "A Persistent Aphid Borne Virus of Soybean, Indonesian *Soybean Dwarf Virus* Transmitted by *Aphis glycines,*" *Plant Dis.* 64:1027-1030.
Kaloshian et al. (1997) "The Impact of the *Meu1*-Mediated Resistance in Tomato on Longevity, Fecundity and Behavior of the Potato Aphid, *Macrosiphum euphorniae,*" *Entomol. Exp. Appl.* 83:181-187.
Keim et al. (1988) "Construction of a Random Recombinant DNA Library that is Primarily Single Copy Sequences," *Soybean Genet. Newslett.* 151:147-148.
Kline, G. (Jun. 8, 2003) "Out of UI Vaults: Bug Resistance," *Champaign-Urbana News-Gazette*.
Klinger et al. (2001) "Mapping of Cotton-Melon Aphid Resistance in Melon," *J. Am. Soc. Hortic. Ci.* 136:56-63.

(Continued)

*Primary Examiner* — Medina A. Ibrahim
*Assistant Examiner* — Keith O. Robinson
(74) *Attorney, Agent, or Firm* — Ellen P. Winner; e winner & associates, pllc

(57) ABSTRACT

*Aphis glycines* resistance (RAG) genes are provided by this invention, along with methods for identifying their presence using marker-assisted selection. Varieties of *G. max* and *G. soja* having resistance to *A. glycines* have been identified. The RAG genes, as well as the methods, aphid-resistant varieties, and markers disclosed herein may be used to breed new elite lines expressing soybean aphid resistance.

7 Claims, 6 Drawing Sheets

OTHER PUBLICATIONS

Li et al. (2004) "Effect of Three Resistant Soybean Genotypes on the Fecundity, Mortality, and Maturation of Soybean Aphid (Homoptera: Aphididae)," *J. Econ Entomol.* 37(3):1106-1111.

Luginbill, J.P. (1969) "Developing Resistant Plants—The Ideal Method of Controlling Insects," USDA, ARS. Prod Res. Rep. 111, USGPO, Washington, D.C.

Mansur et al. (1996) "Genetic Mapping of Agronomic Traits Using Recombinant Inbred Lines of Soybean," *Crop Sci.* 36:1327-1336.

Michelmore et al. (1991) "Identification of Markers Linked to Disease-Resistance Genes by Bulked Segregant Analysis: A Rapid Method to Detect Markers in Specific Genomic Regions by Using Segregating Populations," *Proc. Natl. Acad. Sci. USA* 88:9828-9832.

Narvel et al. (2001) "A Retrospective DNA Marker Assessment of the Development of Insect Resistant Soybean," *Crop Sci.* 41:1931-1939.

NCBI website, http://www.ncbi.nlm.nih.gov/.

Ostile, K. (2002) "Managing Soybean Aphid," http://www.soybeans.umn.edu/crop/insects/aphid/aphid_publication_managingsba.htm.

Patterson et al. (2002) "Assessing and Managing Risk from Soybean Aphids in the North Central States," http://www.planthealth.info/soyaphid/aphid02.htm.

Sama et al. (1974) Research Reports 1968-1974, In, Varietal Screening for Resistance to the Aphid, *Aphis glycines*, in Soybean, Agricultural Cooperation, Indonesia, Netherlands, pp. 171-172.

Sun et al. (1990) "Study on the Uses of Aphid-Resistant Character in Wild Soybean. I. Aphid-Resistance Performance of $F_2$ Generation from Crosses Between Cultivated and Wild Soybeans," *Soybean Genet. News* 17:43-48.

Tyler et al. (1985) "Biotype E Greenbug Resistance in Wheat Streak Mosaic Virus-Resistant Wheat Germplasm Lines," *Crop Sci.* 25:686-688.

Van Ooijen et al. (2001) "Software for the Calculation of Genetic Linkage Maps," JoinMap 3.0, Plant Research International, Wageneingen, the Netherlands.

Wang et al. (1996) "Effects of Soybean Aphid, *Aphis glycines* on Soybean Growth and Yield," *Soybean Sci.* 15:243-247.

Wang et al. (2003) "A Low-Cost, High-Throughput Polyacrylamide Gel Electrophoresis System for Genotyping With Microsatellite DNA Markers," *Crop Sci.* 43:1828-1832.

Wu et al. (2004) "A BAC and BIBAC-based Physical Map of the Soybean Genome," *Genome Res.* 14(2):319-326.

Zhang et al. (2004) "QTL Mapping of Ten Agronomic Traits on the Soybean (*Glycine max* L. Merr.) Genetic Map and Their Association with EST Markers," *Theor. Appl. Genet.* 108:1131-1139.

Zhuang et al. (1996) "A Study on Resistance to Soybean Mosaic Virus and *Aphis glycinece* of Perennial Wild Soybean," *Soybean Genet. Newslett.* 23:66-69.

\* cited by examiner

SEQUENCE LISTING

```
<160> NUMBER OF SEQ ID NOS: 108

<210> SEQ ID NO 1
<211> LENGTH: 894
<212> TYPE: DNA
<213> ORGANISM: Glycine max

<400> SEQUENCE: 1
aagcttctat caagtggtaa tcagagcaca agatcttcaa gtaggtgatc cttaaacctc    60
cattaatttt ttgctttacc ttctcttcta ttgttgtttc ttcattttc tccatgtatc    120 tcctcacatg tcttgtgcta aatgttttta acatgattct ttagagtttc caccgattaa   180
acttgctata gaagctagat ttgattttct atggttcaaa tttcttgttc ttgttcttga   240
tccatgaatt gtgttgagtt taggttcctt tgagttttgt cttgttattt tttgtggctg   300
aaacctaaac cataaaattc ttacaaaaat attaaagtag aggaaaacct caaaaatcta   360
gagtgacttg ttcacctatt atagtttgt catagaagtc atgtctagtc atgaaacttg   420
tcacataaga tttcttatgt tgtgctgaat tttattttct tgtttctttg tctaactcat   480
ttgttcatga gtgtatgaag ttattttagc ctattatttg attggagtca aatctttcat   540
gttaattagt ccttaacatg ttcatgcaaa attcttagag agtctttgat tgtgaacctt   600
ttcttgaact tttaggtttc cttatgattg tgtctattgt gaatttaagt tttggtgatt   660
gaattgctgg ttgaaatgtt gatcctaagt gaatattgaa ctcctaaaac tgtggtaaac   720
aatcctagtg agttcaacat acataggaag gttgaaagta agcccaaggc aatcaatata   780
gcatgcttaa aaaaaaaatc gctggtgctg gcagcttgga catacaaact tgtaaaaatt   840
actgaaaatt ggttacttcg aattttgaac tgaattttta cttaatttgc taga         894

<210> SEQ ID NO 2
<211> LENGTH: 27
<212> TYPE: DNA
<213> ORGANISM: Artificial sequence
<220> FEATURE:
<223> OTHER INFORMATION: Synthetic primer

<400> SEQUENCE: 2
gcgggtagcc atattcatat attgctg                                        27

<210> SEQ ID NO 3
<211> LENGTH: 28
<212> TYPE: DNA
<213> ORGANISM: Artificial sequence
<220> FEATURE:
<223> OTHER INFORMATION: Synthetic primer
```

-continued

```
<400> SEQUENCE: 3
gcgaaggctt ataaggagat acgattta                                           28

<210> SEQ ID NO 4
<211> LENGTH: 18
<212> TYPE: DNA
<213> ORGANISM: Artificial sequence
<220> FEATURE:
<223> OTHER INFORMATION: Synthetic primer

<400> SEQUENCE: 4
tcatccgcca ttgatttt                                                      18

<210> SEQ ID NO 5
<211> LENGTH: 18
<212> TYPE: DNA
<213> ORGANISM: Artificial sequence
<220> FEATURE:
<223> OTHER INFORMATION: Synthetic primer

<400> SEQUENCE: 5
gcccggaaca tacaaaat                                                      18

<210> SEQ ID NO 6
<211> LENGTH: 23
<212> TYPE: DNA
<213> ORGANISM: Artificial sequence
<220> FEATURE:
<223> OTHER INFORMATION: Synthetic primer

<400> SEQUENCE: 6
gcgtaggcat cggtcaatat ttt                                                23

<210> SEQ ID NO 7
<211> LENGTH: 24
<212> TYPE: DNA
<213> ORGANISM: Artificial sequence
<220> FEATURE:
<223> OTHER INFORMATION: Synthetic primer

<400> SEQUENCE: 7
gcgttagcga gtggatcaag atca                                               24

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
tacctttctt gtgagtcgta                                                    20

<210> SEQ ID NO 9
<211> LENGTH: 23
<212> TYPE: DNA
<213> ORGANISM: Artificial sequence
<220> FEATURE:
<223> OTHER INFORMATION: Synthetic primer

<400> SEQUENCE: 9
tattgagatg gatattgtag atc                                                23

<210> SEQ ID NO 10
<211> LENGTH: 24
```

```
<212> TYPE: DNA
<213> ORGANISM: Artificial sequence
<220> FEATURE:
<223> OTHER INFORMATION: Synthetic primer

<400> SEQUENCE: 10
gtcatgactc atgagtcacg taat                                           24

<210> SEQ ID NO 11
<211> LENGTH: 24
<212> TYPE: DNA
<213> ORGANISM: Artificial sequence
<220> FEATURE:
<223> OTHER INFORMATION: Synthetic primer

<400> SEQUENCE: 11
cccaagaccc ccatttttat gtct                                           24

<210> SEQ ID NO 12
<211> LENGTH: 26
<212> TYPE: DNA
<213> ORGANISM: Artificial sequence
<220> FEATURE:
<223> OTHER INFORMATION: Synthetic primer

<400> SEQUENCE: 12
gcgcgcattt tttaagttaa tgttct                                         26

<210> SEQ ID NO 13
<211> LENGTH: 24
<212> TYPE: DNA
<213> ORGANISM: Artificial sequence
<220> FEATURE:
<223> OTHER INFORMATION: Synthetic primer

<400> SEQUENCE: 13
gcgcgagtta gcgaattatt tgtc                                           24

<210> SEQ ID NO 14
<211> LENGTH: 24
<212> TYPE: DNA
<213> ORGANISM: Artificial sequence
<220> FEATURE:
<223> OTHER INFORMATION: Syntehtic primer

<400> SEQUENCE: 14
gcgttgatac tttcctaaga caat                                           24

<210> SEQ ID NO 15
<211> LENGTH: 19
<212> TYPE: DNA
<213> ORGANISM: Artificial sequence
<220> FEATURE:
<223> OTHER INFORMATION: Synthetic primer

<400> SEQUENCE: 15
gggagagaag gcaatctaa                                                 19

<210> SEQ ID NO 16
<211> LENGTH: 25
<212> TYPE: DNA
<213> ORGANISM: Artificial sequence
<220> FEATURE:
<223> OTHER INFORMATION: Synthetic primer

<400> SEQUENCE: 16
aagcttgagg ttattcgaaa atgac                                          25
```

<210> SEQ ID NO 17
<211> LENGTH: 22
<212> TYPE: DNA
<213> ORGANISM: Artificial sequence
<220> FEATURE:
<223> OTHER INFORMATION: Synthetic primer

<400> SEQUENCE: 17
tgccatcagg ttgtgtaagt gt                                          22

<210> SEQ ID NO 18
<211> LENGTH: 25
<212> TYPE: DNA
<213> ORGANISM: Artificial sequence
<220> FEATURE:
<223> OTHER INFORMATION: Synthetic primer

<400> SEQUENCE: 18
gcgcaacgtc taaagcacaa ggatt                                       25

<210> SEQ ID NO 19
<211> LENGTH: 23
<212> TYPE: DNA
<213> ORGANISM: Artificial sequence
<220> FEATURE:
<223> OTHER INFORMATION: Synthetic primer

<400> SEQUENCE: 19
gcgcgactac gttacagttc caa                                         23

<210> SEQ ID NO 20
<211> LENGTH: 18
<212> TYPE: DNA
<213> ORGANISM: Artificial sequence
<220> FEATURE:
<223> OTHER INFORMATION: Synthetic primer

<400> SEQUENCE: 20
ggctaacccg ctctatgt                                               18

<210> SEQ ID NO 21
<211> LENGTH: 19
<212> TYPE: DNA
<213> ORGANISM: Artificial sequence
<220> FEATURE:
<223> OTHER INFORMATION: Synthetic primer

<400> SEQUENCE: 21
gggccatgca cctgctact                                              19

<210> SEQ ID NO 22
<211> LENGTH: 22
<212> TYPE: DNA
<213> ORGANISM: Artificial sequence
<220> FEATURE:
<223> OTHER INFORMATION: Synthetic primer

<400> SEQUENCE: 22
ctggcgaatc aagctttgta ac                                          22

<210> SEQ ID NO 23
<211> LENGTH: 22
<212> TYPE: DNA
<213> ORGANISM: Artificial sequence
<220> FEATURE:
<223> OTHER INFORMATION: Synthetic primer

```
<400> SEQUENCE: 23
ccgtgattgc gaagaggata tt                                                22

<210> SEQ ID NO 24
<211> LENGTH: 28
<212> TYPE: DNA
<213> ORGANISM: Artificial sequence
<220> FEATURE:
<223> OTHER INFORMATION: Synthetic primer

<400> SEQUENCE: 24
gcggtgaaac ggctctcttt gatagtga                                          28

<210> SEQ ID NO 25
<211> LENGTH: 28
<212> TYPE: DNA
<213> ORGANISM: Artificial sequence
<220> FEATURE:
<223> OTHER INFORMATION: Synthetic primer

<400> SEQUENCE: 25
gcgttggatt aattaattaa attatttt                                          28

<210> SEQ ID NO 26
<211> LENGTH: 23
<212> TYPE: DNA
<213> ORGANISM: Artificial sequence
<220> FEATURE:
<223> OTHER INFORMATION: Synthetic primer

<400> SEQUENCE: 26
gcgtcaaccg gtgaaaaaac cta                                               23

<210> SEQ ID NO 27
<211> LENGTH: 25
<212> TYPE: DNA
<213> ORGANISM: Artificial sequence
<220> FEATURE:
<223> OTHER INFORMATION: Synthetic primer

<400> SEQUENCE: 27
gcgtggctgg cagtagtcta tatca                                             25

<210> SEQ ID NO 28
<211> LENGTH: 26
<212> TYPE: DNA
<213> ORGANISM: Artificial sequence
<220> FEATURE:
<223> OTHER INFORMATION: Synthetic primer

<400> SEQUENCE: 28
ttggatctca tattcaaact ttcaag                                            26

<210> SEQ ID NO 29
<211> LENGTH: 26
<212> TYPE: DNA
<213> ORGANISM: Artificial sequence
<220> FEATURE:
<223> OTHER INFORMATION: Synthetic primer

<400> SEQUENCE: 29
ctgcaaattt gatgcacatg tgtcta                                            26

<210> SEQ ID NO 30
<211> LENGTH: 29
```

```
<212> TYPE: DNA
<213> ORGANISM: Artificial sequence
<220> FEATURE:
<223> OTHER INFORMATION: Synthetic primer

<400> SEQUENCE: 30
gcgattggtt gggtgtttaa ttttaagat                                       29

<210> SEQ ID NO 31
<211> LENGTH: 30
<212> TYPE: DNA
<213> ORGANISM: Artificial sequence
<220> FEATURE:
<223> OTHER INFORMATION: Synthetic primer

<400> SEQUENCE: 31
gcgtgttgat ggtataaaga tcgctactct                                      30

<210> SEQ ID NO 32
<211> LENGTH: 22
<212> TYPE: DNA
<213> ORGANISM: Artificial sequence
<220> FEATURE:
<223> OTHER INFORMATION: Synthetic primer

<400> SEQUENCE: 32
aacgggagta ggacatttta tt                                              22

<210> SEQ ID NO 33
<211> LENGTH: 28
<212> TYPE: DNA
<213> ORGANISM: Artificial sequence
<220> FEATURE:
<223> OTHER INFORMATION: Synthetic primer

<400> SEQUENCE: 33
gcgcctcctg aatttcaaag aatgaaga                                        28

<210> SEQ ID NO 34
<211> LENGTH: 23
<212> TYPE: DNA
<213> ORGANISM: Artificial sequence
<220> FEATURE:
<223> OTHER INFORMATION: Synthetic primer

<400> SEQUENCE: 34
gaggaggatc ccaaggtaat aat                                             23

<210> SEQ ID NO 35
<211> LENGTH: 20
<212> TYPE: DNA
<213> ORGANISM: Artificial sequence
<220> FEATURE:
<223> OTHER INFORMATION: Synthetic primer

<400> SEQUENCE: 35
gcgcatggag aaaagaagag                                                 20

<210> SEQ ID NO 36
<211> LENGTH: 27
<212> TYPE: DNA
<213> ORGANISM: Artificial sequence
<220> FEATURE:
<223> OTHER INFORMATION: Synthetic primer

<400> SEQUENCE: 36
gcggatggag acgggggca cggacga                                          27
```

<210> SEQ ID NO 37
<211> LENGTH: 27
<212> TYPE: DNA
<213> ORGANISM: Artificial sequence
<220> FEATURE:
<223> OTHER INFORMATION: Synthetic primer

<400> SEQUENCE: 37
gcgcatagct aattttatat caattat                                27

<210> SEQ ID NO 38
<211> LENGTH: 24
<212> TYPE: DNA
<213> ORGANISM: Artificial sequence
<220> FEATURE:
<223> OTHER INFORMATION: Synthetic primer

<400> SEQUENCE: 38
gcggtcgtcc tatctaatga agag                                   24

<210> SEQ ID NO 39
<211> LENGTH: 24
<212> TYPE: DNA
<213> ORGANISM: Artificial sequence
<220> FEATURE:
<223> OTHER INFORMATION: Synthetic primer

<400> SEQUENCE: 39
tgtgcgttta aattgcagct aaat                                   24

<210> SEQ ID NO 40
<211> LENGTH: 30
<212> TYPE: DNA
<213> ORGANISM: Artificial sequence
<220> FEATURE:
<223> OTHER INFORMATION: Synthetic primer

<400> SEQUENCE: 40
gcgcaataga taatcgaaaa acatacaaga                             30

<210> SEQ ID NO 41
<211> LENGTH: 28
<212> TYPE: DNA
<213> ORGANISM: Artificial sequence
<220> FEATURE:
<223> OTHER INFORMATION: Synthetic primer

<400> SEQUENCE: 41
gcggggaaag tgaaaacaag atcaaata                               28

<210> SEQ ID NO 42
<211> LENGTH: 21
<212> TYPE: DNA
<213> ORGANISM: Artificial sequence
<220> FEATURE:
<223> OTHER INFORMATION: Synthetic primer

<400> SEQUENCE: 42
gcggggttct gtggcttcaa c                                      21

<210> SEQ ID NO 43
<211> LENGTH: 21
<212> TYPE: DNA
<213> ORGANISM: Artificial sequence
<220> FEATURE:
<223> OTHER INFORMATION: Synthetic primer

<400> SEQUENCE: 43
gcgcattgga ataacgtcaa a                                          21

<210> SEQ ID NO 44
<211> LENGTH: 24
<212> TYPE: DNA
<213> ORGANISM: Artificial sequence
<220> FEATURE:
<223> OTHER INFORMATION: Synthetic primer

<400> SEQUENCE: 44
gcgccacaga aattccttttt tcta                                      24

<210> SEQ ID NO 45
<211> LENGTH: 25
<212> TYPE: DNA
<213> ORGANISM: Artificial sequence
<220> FEATURE:
<223> OTHER INFORMATION: Synthetic primer

<400> SEQUENCE: 45
gcgccataag gtggttacca aaaga                                      25

<210> SEQ ID NO 46
<211> LENGTH: 20
<212> TYPE: DNA
<213> ORGANISM: Artificial sequence
<220> FEATURE:
<223> OTHER INFORMATION: Synthetic primer

<400> SEQUENCE: 46
tgatttttgg tgtagaactc                                            20

<210> SEQ ID NO 47
<211> LENGTH: 21
<212> TYPE: DNA
<213> ORGANISM: Artificial sequence
<220> FEATURE:
<223> OTHER INFORMATION: Synthetic primer

<400> SEQUENCE: 47
caaattggtt agcttactcc a                                          21

<210> SEQ ID NO 48
<211> LENGTH: 22
<212> TYPE: DNA
<213> ORGANISM: Artificial sequence
<220> FEATURE:
<223> OTHER INFORMATION: Synthetic primer

<400> SEQUENCE: 48
gcggagtttc ccctaattag at                                         22

<210> SEQ ID NO 49
<211> LENGTH: 26
<212> TYPE: DNA
<213> ORGANISM: Artificial sequence
<220> FEATURE:
<223> OTHER INFORMATION: Synthetic primer

<400> SEQUENCE: 49
gcgcaagcta gcttcaccca aaacta                                     26

<210> SEQ ID NO 50
<211> LENGTH: 29

```
<212> TYPE: DNA
<213> ORGANISM: Artificial sequence
<220> FEATURE:
<223> OTHER INFORMATION: Synthetic primer

<400> SEQUENCE: 50
gcggaaaccc acctatatgt gatcaaatg                                29

<210> SEQ ID NO 51
<211> LENGTH: 30
<212> TYPE: DNA
<213> ORGANISM: Artificial sequence
<220> FEATURE:
<223> OTHER INFORMATION: Synthetic primer

<400> SEQUENCE: 51
gcgcaattcc agatgaaaca gaagaaggat                               30

<210> SEQ ID NO 52
<211> LENGTH: 22
<212> TYPE: DNA
<213> ORGANISM: Artificial sequence
<220> FEATURE:
<223> OTHER INFORMATION: Synthetic primer

<400> SEQUENCE: 52
gacctcgctc tctgtttctc at                                       22

<210> SEQ ID NO 53
<211> LENGTH: 22
<212> TYPE: DNA
<213> ORGANISM: Artificial sequence
<220> FEATURE:
<223> OTHER INFORMATION: Synthetic primer

<400> SEQUENCE: 53
ggtgaccacc cctattcctt at                                       22

<210> SEQ ID NO 54
<211> LENGTH: 24
<212> TYPE: DNA
<213> ORGANISM: Artificial sequence
<220> FEATURE:
<223> OTHER INFORMATION: Synthetic primer

<400> SEQUENCE: 54
ggccggttct cattacaggt ctct                                     24

<210> SEQ ID NO 55
<211> LENGTH: 24
<212> TYPE: DNA
<213> ORGANISM: Artificial sequence
<220> FEATURE:
<223> OTHER INFORMATION: Synthetic primer

<400> SEQUENCE: 55
ggatttccat cttgaatttt atta                                     24

<210> SEQ ID NO 56
<211> LENGTH: 17
<212> TYPE: DNA
<213> ORGANISM: Artificial sequence
<220> FEATURE:
<223> OTHER INFORMATION: Synthetic primer

<400> SEQUENCE: 56
tctcgactca cgactca                                             17
```

<210> SEQ ID NO 57
<211> LENGTH: 17
<212> TYPE: DNA
<213> ORGANISM: Artificial sequence
<220> FEATURE:
<223> OTHER INFORMATION: Synthetic primer

<400> SEQUENCE: 57
ccaaggtctc tcagagg                                                    17

<210> SEQ ID NO 58
<211> LENGTH: 28
<212> TYPE: DNA
<213> ORGANISM: Artificial sequence
<220> FEATURE:
<223> OTHER INFORMATION: Synthetic primer

<400> SEQUENCE: 58
gcgcggaaaa ttattttact ttttcaat                                        28

<210> SEQ ID NO 59
<211> LENGTH: 28
<212> TYPE: DNA
<213> ORGANISM: Artificial sequence
<220> FEATURE:
<223> OTHER INFORMATION: Synthetic primer

<400> SEQUENCE: 59
gcgcacggat tgagagaaag cagaaaga                                        28

<210> SEQ ID NO 60
<211> LENGTH: 22
<212> TYPE: DNA
<213> ORGANISM: Artificial sequence
<220> FEATURE:
<223> OTHER INFORMATION: Synthetic primer

<400> SEQUENCE: 60
caacgaccaa ctgacgagac ct                                              22

<210> SEQ ID NO 61
<211> LENGTH: 24
<212> TYPE: DNA
<213> ORGANISM: Artificial sequence
<220> FEATURE:
<223> OTHER INFORMATION: Synthetic primer

<400> SEQUENCE: 61
gggaattcaa catgtgatgg tttt                                            24

<210> SEQ ID NO 62
<211> LENGTH: 30
<212> TYPE: DNA
<213> ORGANISM: Artificial sequence
<220> FEATURE:
<223> OTHER INFORMATION: Synthetic primer

<400> SEQUENCE: 62
gcgacagact gcaagaattg atgtaaatct                                      30

<210> SEQ ID NO 63
<211> LENGTH: 31
<212> TYPE: DNA
<213> ORGANISM: Artificial sequence
<220> FEATURE:
<223> OTHER INFORMATION: Synthetic primer

<400> SEQUENCE: 63
gcgggaaggt aggtaaagaa aattcaaatg a                               31

<210> SEQ ID NO 64
<211> LENGTH: 24
<212> TYPE: DNA
<213> ORGANISM: Artificial sequence
<220> FEATURE:
<223> OTHER INFORMATION: Synthetic primer

<400> SEQUENCE: 64
gaagaccaaa acttatttca gatc                                       24

<210> SEQ ID NO 65
<211> LENGTH: 22
<212> TYPE: DNA
<213> ORGANISM: Artificial sequence
<220> FEATURE:
<223> OTHER INFORMATION: Synthetic primer

<400> SEQUENCE: 65
attttaagca ccagcaaaga ct                                         22

<210> SEQ ID NO 66
<211> LENGTH: 26
<212> TYPE: DNA
<213> ORGANISM: Artificial sequence
<220> FEATURE:
<223> OTHER INFORMATION: Synthetic primer

<400> SEQUENCE: 66
gcgggatatc gtgagcatag ttttac                                     26

<210> SEQ ID NO 67
<211> LENGTH: 28
<212> TYPE: DNA
<213> ORGANISM: Artificial sequence
<220> FEATURE:
<223> OTHER INFORMATION: Synthetic primer

<400> SEQUENCE: 67
gcggcctgaa tattttaggt ttagagtt                                   28

<210> SEQ ID NO 68
<211> LENGTH: 24
<212> TYPE: DNA
<213> ORGANISM: Artificial sequence
<220> FEATURE:
<223> OTHER INFORMATION: Synthetic primer

<400> SEQUENCE: 68
gcgtattttg ggggattttg aaca                                       24

<210> SEQ ID NO 69
<211> LENGTH: 25
<212> TYPE: DNA
<213> ORGANISM: Artificial sequence
<220> FEATURE:
<223> OTHER INFORMATION: Synthetic primer

<400> SEQUENCE: 69
gcgtttctct tcttattctt tctct                                      25

<210> SEQ ID NO 70
<211> LENGTH: 17

```
<212> TYPE: DNA
<213> ORGANISM: Artificial sequence
<220> FEATURE:
<223> OTHER INFORMATION: Synthetic primer

<400> SEQUENCE: 70
gcgaaatgcc gaaagag                                                       17

<210> SEQ ID NO 71
<211> LENGTH: 20
<212> TYPE: DNA
<213> ORGANISM: Artificial sequence
<220> FEATURE:
<223> OTHER INFORMATION: Synthetic primer

<400> SEQUENCE: 71
gcggggataa gaaaaacaat                                                    20

<210> SEQ ID NO 72
<211> LENGTH: 23
<212> TYPE: DNA
<213> ORGANISM: Artificial sequence
<220> FEATURE:
<223> OTHER INFORMATION: Synthetic primer

<400> SEQUENCE: 72
gcgcttaagg acacggatgt aac                                                23

<210> SEQ ID NO 73
<211> LENGTH: 25
<212> TYPE: DNA
<213> ORGANISM: Artificial sequence
<220> FEATURE:
<223> OTHER INFORMATION: Synthetic primer

<400> SEQUENCE: 73
gcgtctcttt cgattgttct attag                                              25

<210> SEQ ID NO 74
<211> LENGTH: 28
<212> TYPE: DNA
<213> ORGANISM: Artificial sequence
<220> FEATURE:
<223> OTHER INFORMATION: Synthetic primer

<400> SEQUENCE: 74
gcgtacccct atatggatgt ttcttcct                                           28

<210> SEQ ID NO 75
<211> LENGTH: 29
<212> TYPE: DNA
<213> ORGANISM: Artificial sequence
<220> FEATURE:
<223> OTHER INFORMATION: Synthetic primer

<400> SEQUENCE: 75
gcgtatgcag caaacaaaaa atatataat                                          29

<210> SEQ ID NO 76
<211> LENGTH: 21
<212> TYPE: DNA
<213> ORGANISM: Artificial sequence
<220> FEATURE:
<223> OTHER INFORMATION: Synthetic primer

<400> SEQUENCE: 76
gcgttttcct aatgaagatt t                                                  21
```

<210> SEQ ID NO 77
<211> LENGTH: 23
<212> TYPE: DNA
<213> ORGANISM: Artificial sequence
<220> FEATURE:
<223> OTHER INFORMATION: Synthetic primer

<400> SEQUENCE: 77
gcgtgtaata gtgatggatg taa                                         23

<210> SEQ ID NO 78
<211> LENGTH: 23
<212> TYPE: DNA
<213> ORGANISM: Artificial sequence
<220> FEATURE:
<223> OTHER INFORMATION: Synthetic primer

<400> SEQUENCE: 78
gcgtgcttta aatgattgat tga                                         23

<210> SEQ ID NO 79
<211> LENGTH: 23
<212> TYPE: DNA
<213> ORGANISM: Artificial sequence
<220> FEATURE:
<223> OTHER INFORMATION: Synthetic primer

<400> SEQUENCE: 79
gcgtgcgaac ataactaata cat                                         23

<210> SEQ ID NO 80
<211> LENGTH: 22
<212> TYPE: DNA
<213> ORGANISM: Artificial sequence
<220> FEATURE:
<223> OTHER INFORMATION: Synthetic primer

<400> SEQUENCE: 80
gaatatcacg cgagaatttt ac                                          22

<210> SEQ ID NO 81
<211> LENGTH: 22
<212> TYPE: DNA
<213> ORGANISM: Artificial sequence
<220> FEATURE:
<223> OTHER INFORMATION: Synthetic primer

<400> SEQUENCE: 81
tatatgcgaa ccctcttaca at                                          22

<210> SEQ ID NO 82
<211> LENGTH: 30
<212> TYPE: DNA
<213> ORGANISM: Artificial sequence
<220> FEATURE:
<223> OTHER INFORMATION: Synthetic primer

<400> SEQUENCE: 82
gacaaatgta aaagtgaca gatagaatgt                                   30

<210> SEQ ID NO 83
<211> LENGTH: 28
<212> TYPE: DNA
<213> ORGANISM: Artificial sequence
<220> FEATURE:
<223> OTHER INFORMATION: Synthetic primer

```
<400> SEQUENCE: 83
gtgtggtggt ggtacagttt tatactaa                                          28

<210> SEQ ID NO 84
<211> LENGTH: 20
<212> TYPE: DNA
<213> ORGANISM: Artificial sequence
<220> FEATURE:
<223> OTHER INFORMATION: Synthetic primer

<400> SEQUENCE: 84
cgccagctag ctagtctcat                                                   20

<210> SEQ ID NO 85
<211> LENGTH: 24
<212> TYPE: DNA
<213> ORGANISM: Artificial sequence
<220> FEATURE:
<223> OTHER INFORMATION: Synthetic primer

<400> SEQUENCE: 85
aatttgctcc agtgttttaa gttt                                              24

<210> SEQ ID NO 86
<211> LENGTH: 27
<212> TYPE: DNA
<213> ORGANISM: Artificial sequence
<220> FEATURE:
<223> OTHER INFORMATION: Synthetic primer

<400> SEQUENCE: 86
gcggtgatat taccccaaaa aaatgaa                                           27

<210> SEQ ID NO 87
<211> LENGTH: 27
<212> TYPE: DNA
<213> ORGANISM: Artificial sequence
<220> FEATURE:
<223> OTHER INFORMATION: Synthetic primer

<400> SEQUENCE: 87
gcgctagttt ctagtggaaa gatgagt                                           27

<210> SEQ ID NO 88
<211> LENGTH: 28
<212> TYPE: DNA
<213> ORGANISM: Artificial sequence
<220> FEATURE:
<223> OTHER INFORMATION: Synthetic primer

<400> SEQUENCE: 88
gcgaaaaacg tcaggtcaat gactgaaa                                          28

<210> SEQ ID NO 89
<211> LENGTH: 28
<212> TYPE: DNA
<213> ORGANISM: Artificial sequence
<220> FEATURE:
<223> OTHER INFORMATION: Synthetic primer

<400> SEQUENCE: 89
gcggggctta gatataaaaa aaaagatg                                          28

<210> SEQ ID NO 90
<211> LENGTH: 21
```

```
<212> TYPE: DNA
<213> ORGANISM: Artificial sequence
<220> FEATURE:
<223> OTHER INFORMATION: Synthetic primer

<400> SEQUENCE: 90
ggagggagga aagtgttgtg g                                        21

<210> SEQ ID NO 91
<211> LENGTH: 21
<212> TYPE: DNA
<213> ORGANISM: Artificial sequence
<220> FEATURE:
<223> OTHER INFORMATION: Synthetic primer

<400> SEQUENCE: 91
gcgcatgctt ttcataagtt t                                        21

<210> SEQ ID NO 92
<211> LENGTH: 24
<212> TYPE: DNA
<213> ORGANISM: Artificial sequence
<220> FEATURE:
<223> OTHER INFORMATION: Synthetic priemr

<400> SEQUENCE: 92
gtgcgacgtc atgccttact caat                                     24

<210> SEQ ID NO 93
<211> LENGTH: 24
<212> TYPE: DNA
<213> ORGANISM: Artificial sequence
<220> FEATURE:
<223> OTHER INFORMATION: Synthetic primer

<400> SEQUENCE: 93
gcgctccgta cacttaaaaa agaa                                     24

<210> SEQ ID NO 94
<211> LENGTH: 29
<212> TYPE: DNA
<213> ORGANISM: Artificial sequence
<220> FEATURE:
<223> OTHER INFORMATION: Synthetic primer

<400> SEQUENCE: 94
gcggaaaccc atctagaata tgaaaaaca                                29

<210> SEQ ID NO 95
<211> LENGTH: 27
<212> TYPE: DNA
<213> ORGANISM: Artificial sequence
<220> FEATURE:
<223> OTHER INFORMATION: Synthetic primer

<400> SEQUENCE: 95
gcgttcttct cgaggtgaga tacaatc                                  27

<210> SEQ ID NO 96
<211> LENGTH: 26
<212> TYPE: DNA
<213> ORGANISM: Artificial sequence
<220> FEATURE:
<223> OTHER INFORMATION: Synthetic primer

<400> SEQUENCE: 96
gcgttaaggt tggcagggtg gaagtg                                   26
```

```
<210> SEQ ID NO 97
<211> LENGTH: 26
<212> TYPE: DNA
<213> ORGANISM: Artificial sequence
<220> FEATURE:
<223> OTHER INFORMATION: Synthetic primer

<400> SEQUENCE: 97
gcgcagcttt atacaaaaat caacaa                                              26

<210> SEQ ID NO 98
<211> LENGTH: 18
<212> TYPE: DNA
<213> ORGANISM: Artificial sequence
<220> FEATURE:
<223> OTHER INFORMATION: Synthetic primer

<400> SEQUENCE: 98
aattggagtg ggtcacac                                                       18

<210> SEQ ID NO 99
<211> LENGTH: 18
<212> TYPE: DNA
<213> ORGANISM: Artificial sequence
<220> FEATURE:
<223> OTHER INFORMATION: Synthetic primer

<400> SEQUENCE: 99
ttcccggaaa gaaagaaa                                                       18

<210> SEQ ID NO 100
<211> LENGTH: 31
<212> TYPE: DNA
<213> ORGANISM: Artificial sequence
<220> FEATURE:
<223> OTHER INFORMATION: Synthetic primer

<400> SEQUENCE: 100
gcgggtcacg attctagtca ctataacttc a                                        31

<210> SEQ ID NO 101
<211> LENGTH: 30
<212> TYPE: DNA
<213> ORGANISM: Artificial sequence
<220> FEATURE:
<223> OTHER INFORMATION: Synthetic primer

<400> SEQUENCE: 101
gcgcaacgta agaaatgtaa atacaatgga                                          30

<210> SEQ ID NO 102
<211> LENGTH: 26
<212> TYPE: DNA
<213> ORGANISM: Artificial sequence
<220> FEATURE:
<223> OTHER INFORMATION: Synthetic primer

<400> SEQUENCE: 102
gcgttaggat ttaggatgag gatagg                                              26

<210> SEQ ID NO 103
<211> LENGTH: 26
<212> TYPE: DNA
<213> ORGANISM: Artificial sequence
<220> FEATURE:
<223> OTHER INFORMATION: Synthetic primer
```

<400> SEQUENCE: 103
gcgcaaatca gttgagcaat gactta                                             26

<210> SEQ ID NO 104
<211> LENGTH: 10
<212> TYPE: DNA
<213> ORGANISM: Artificial sequence
<220> FEATURE:
<223> OTHER INFORMATION: Synthetic priemr

<400> SEQUENCE: 104
accaggttgg                                                               10

<210> SEQ ID NO 105
<211> LENGTH: 797
<212> TYPE: DNA
<213> ORGANISM: Glycine max
<220> FEATURE:
<221> NAME/KEY: misc_feature
<222> LOCATION: (1)..(797)
<223> OTHER INFORMATION: N is A, T, G or C.

<400> SEQUENCE: 105
tatcattata ttgcaggcta cnnaaatttc cagtnntaat acagtataat taagcagagt        60
gtggtatcta caaaatctca atccaaacac ataattacaa aactctagaa cagcagaaca       120
catatagcat ttgatttgaa gtattcattc actaattgat tagccttaga aattcaaatg       180
atataatctg accactcaga gataaaggaa gtatggtcca tggactcccc aggaacatcc       240
tcgtgcttag agggcttctc cttcccacca accaacctgg ctgggttccc aacagctgtt       300
gtctgtggtg gcacatcgat taaaaccacc gagccagcac aacctttgca ccttccccga       360
tcttaatatt ccccagaatg gtagcaccgg caccaataag cacccccatcc ccaatcttgg       420
gatgccggtc cccaccaact tgccagtccc acccagcgta acgtggtgca ggatcgacac       480
attgttccga tcactgccgt ctcccccacc accaccccgg tggcatggtc gaacagatcc       540
ccttcccgat cctcgccgca gggtgaatgt ccaccgcgaa cacatcgcga tgcgagagtg       600
cagtgcnaaa gccaatggct gccgcgattg ncgnccaaca gatgcgccac acggtgcgcc       660
tgcaaaatca caatcacaca caactaatcc taagattcaa taatcaaaaa agagtnnact       720
nnncatacac tgtcatcncn nntatagtca tgtttcatnn naatctngnn nnacaatgca       780
tataaattaa actcaat                                                     797

<210> SEQ ID NO 106
<211> LENGTH: 701
<212> TYPE: DNA
<213> ORGANISM: Glycine max
<220> FEATURE:
<221> NAME/KEY: misc_feature
<222> LOCATION: (1)..(701)
<223> OTHER INFORMATION: N is A, T, G or C.

<400> SEQUENCE: 106
aaagnnaaca tttttgttta tatgacnnna acaaactgca agaaaaaatt gttaaaaacc        60
agaagcaatt taggtgatca caaataccac atgcttacac cttccagtga caagtacagt       120
atgttgtggc accagccgtt tcagttgatg caaacttgct tcgtgccaaa attctaacaa       180
cacaactacc taagctatca aacaagagaa gcccttttgt cctttggtcg acctatcaaa       240
ggtcatcaga tcacactagt cctaccctttt aagaaaacc tactatcaac agtcatatgt       300
atctcatgaa aagcacataa aaacatgtca ctttgcctct tcaccatctc cactgttatg       360

| | |
|---|---|
| agcagccgcg gagctgcctt ggccgtctcc accagctgtt ccagcctcag aggcatcttg | 420 |
| cttgcttcca ccacgtgcat cgtttggacc agtagccgaa ggtggaccac cgctgtttcc | 480 |
| cctccaagag cagcctcact gtgcattgga tgcatgccat tatttatatc tccaggtcta | 540 |
| agtcccattt gaccttggat ggcctgctgg tgtagctgct gttgttgttc ctgcatttga | 600 |
| tgtggattgc caaattgcaa tggcattttc tgggggaaca nnccttgctg ctgctgnnnn | 660 |
| attgctgctg cagcnnnntg nnnatnnnnn atatannnnn c | 701 |

<210> SEQ ID NO 107
<211> LENGTH: 799
<212> TYPE: DNA
<213> ORGANISM: Glycine max
<220> FEATURE:
<221> NAME/KEY: misc_feature
<222> LOCATION: (1)..(799)
<223> OTHER INFORMATION: N is A, T, G or C.

<400> SEQUENCE: 107

| | |
|---|---|
| tatcattata ttgcaggcta cnnaaatttc cagtnntaat acagtataat taagcagagt | 60 |
| gtggtatcta caaaatctca atccaaacac ataattacaa aactctagaa cagcagaaca | 120 |
| catatagcat ttgatttgaa gtattcattc actaattgat tagccttaga aattcaaatg | 180 |
| atataatctg accactcaga gataaaggaa gtatggtcca tggactcccc aggaacatcc | 240 |
| tcgtgcttag agggcttctc cttcccacca accaacctgg ctgggttccc aacagctgtt | 300 |
| gtctgtggtg gcacatcgat taaaaccacc gagccagcac caacctttgc accttccccg | 360 |
| atcttaatat tccccagaat ggtagcaccg gcaccaataa gcaccccatc cccaatcttg | 420 |
| ggatgccggt cccaccaac cttgccagtc acccagcgt aacgtggtgc aggatcgaca | 480 |
| cattgttccc gatcactgcc gtctccccca ccaccaccc ggtggcatgg tcgaacagaa | 540 |
| tccccttccg atcctcgccg cagggtgaat gtccaccgcg aacacatcag cgatgcgaag | 600 |
| tgcagtgcna agccaatgg ctgccgcgat tgncgncaca acagatggcc acacggtgcg | 660 |
| cctgcaaaat cacaatcaca cacaactaat cctaagattc aataatcaaa aaagagtnna | 720 |
| ctnnncatac actgtcatcn cnnntatagt catgtttcat nnnaatctng nnnnacaatg | 780 |
| catataaatt aaactcaat | 799 |

<210> SEQ ID NO 108
<211> LENGTH: 702
<212> TYPE: DNA
<213> ORGANISM: Glycine max
<220> FEATURE:
<221> NAME/KEY: misc_feature
<222> LOCATION: (1)..(702)
<223> OTHER INFORMATION: N is A, T, G or C.

<400> SEQUENCE: 108

| | |
|---|---|
| aagacannnn cgttacataa tcctcacata tagtcatcca atcagaactg aataggaaaa | 60 |
| aaaaatacac aatattaatg aaatttaatt tatcatctgc atgtttggat aagcgtcaaa | 120 |
| ggtaaaccta ctattagtag cttttcttgtc tttccttcaa tttgacgtga ttttagtttg | 180 |
| agacgtgcat gtataaagtg gatccaaaca cactattatg gtatgcagag tgaagtaaaa | 240 |
| acttaaaaat cagagcagcg accattgcgt tcccagtcac cataccagt gggctcaggc | 300 |
| ccttgggtcc accaatctca cctgtttctt tgttaatact gtcaccatct tcgtggtctt | 360 |
| cttcgggctc atggctttgt tgttctcat catggagaga ttcttgaggt ggtgtctgtg | 420 |
| cttgttccct gagngggttt tcgtgttgtg gctgagttga agagcagnng agccgtgtca | 480 |

-continued

```
ctgtgttgga aacaaaatgg taaactgctc ggatttggtg cggtgannnn cnntgttggc    540
tacacaagca gtgagcgagg gaannnggtg gtcattgttg tttgttaatg atgtaaggca    600
gatgatcaga aannagaaaa ctcgtancnn nacgaacaaa accctgaaat ggtttaaagc    660
tnnnccttgg attttgattc ttgttgctgc gcgttngnnt gc                      702
```

SOYBEAN GENES FOR RESISTANCE TO *APHIS GLYCINES*

CROSS-REFERENCE TO RELATED APPLICATIONS

This application claims priority to U.S. Provisional Application No. 60/581,501 filed Jun. 21, 2004, which is incorporated by reference herein to the extent not inconsistent herewith.

BACKGROUND OF THE INVENTION

This invention relates to a soybean gene for resistance to *Aphis glycines*, to soybean plants possessing this gene, which maps to a novel chromosomal locus, and to methods for identifying and breeding these plants, the methods involving marker-assisted selection.

Soybeans (*Glycine max* L. Merr.) are a major cash crop and investment commodity in North America and elsewhere. Soybean oil is one of the most widely used edible oils, and soybeans are used worldwide both in animal feed and in human food production.

A native of Asia, the soybean aphid was first found in the Midwest in 2000 (Hartman, G. L. et al., "Occurrence and distribution of *Aphis glycines* on soybeans in Illinois in 2000 and its potential control," (1 Feb. 2001 available at a website address beginning with the usual http and www prefixes, followed by plantmanagementnetwork.org/php/default, followed by the suffix .asp.) It rapidly spread throughout the region and into other parts of North America (Patterson, J. and Ragsdale, D., "Assessing and managing risk from soybean aphids in the North Central States," (11 Apr. 2002) available at a website address beginning with the usual http and www prefixes, followed by planthealth.info/soyaphid/aphid02, followed by the suffix .htm.) High aphid populations can reduce crop production directly when their feeding causes severe damage such as stunting, leaf distortion, and reduced pod set (Sun, Z. et al., "Study on the uses of aphid-resistant character in wild soybean. I. Aphid-resistance performance of $F_2$ generation from crosses between cultivated and wild soybeans," (1990) *Soybean Genet. News*. 17:43-48). Yield losses attributed to the aphid in some fields in Minnesota during 2001, where several thousand aphids occurred on individual soybean plants, were >50% (Ostlie, K., "Managing soybean aphid," (2 Oct. 2002) available at a website having an address beginning with the usual http and www, followed by soybeans.umn.edu/crop/insects/aphid/aphid_publication_managingsba, and having a suffix .htm) with an average loss of 101 to 202 kg ha$^{-1}$ in those fields (Patterson and Ragsdale, supra). In earlier reports from China, soybean yields were reduced up to 52% when there was an average of about 220 aphids per plant (Wang, X. B. et al., "A study on the damage and economic threshold of the soybean aphid at the seedling stage," (1994) *Plant Prot.* (China) 20:12-13) and plant height was decreased by about 210 mm after severe aphid infestation (Wang, X. B. et al., "Study on the effects of the population dynamics of soybean aphid (*Aphis glycines*) on both growth and yield of soybean," (1996) *Soybean Sci*. 15:243-247). An additional threat posed by the aphid is its ability to transmit certain plant viruses to soybean such as Alfalfa mosaic virus, Soybean dwarf virus, and Soybean mosaic virus (Sama, S. et al., "Varietal screening for resistance to the aphid, *Aphis glycines*, in soybean," (1974) *Research Reports* 1968-1974, pp. 171-172; Iwaki, M. et al., "A persistent aphid borne virus of soybean, Indonesian Soybean dwarf virus transmitted by *Aphis glycines*," (1980) *Plant Dis*. 64:1027-1030; Hartman, G. L. et al., supra; Hill, J. H. et al., "First report of transmission of Soybean mosaic virus and Alfalfa mosaic virus by *Aphis glycines* (Homoptera, Aphididae)," (1996) *Appl. Entomol. Zool*. 31:178-180; Clark, A. J. and Perry, K. L., "Transmissibility of field isolates of soybean viruses by *Aphis glycines*," (2002) *Plant Dis*. 86:1219-1222).

Because *A. glycines* is a recent pest in the USA, a comprehensive integrated management approach to control the aphid has yet to be developed. Research to evaluate the efficacy of currently-available insecticides and other control measures has just begun.

An integral component of an integrated pest management (IPM) program to control aphids is plant resistance (Auclair, J. L., "Host plant resistance," pp. 225-265 In P. Harrewijn (ed.) *Aphids: Their biology, natural enemies, and control*, Vol. C., Elsevier, N.Y. (1989); Harrewijn, P. and Minks, A. K., "Integrated aphid management: General aspects," pp. 267-272, In A. K. Minks and P. Harrewijn (ed.) *Aphids: Their biology, natural enemies, and control*, Vol. C., Elsevier, N.Y. (1989). Insect resistance can significantly reduce input costs for producers (Luginbill, J. P., "Developing resistant plants—The ideal method of controlling insects," (1969) USDA, ARS. Prod. Res. Rep. 111, USGPO, Washington, D.C. Resistance was reported in *G. soja* (Sun, Z. et al., "Study on the uses of aphid-resistant character in wild soybean. I. Aphid-resistance performance of $F_2$ generation from crosses between cultivated and wild soybeans," (1990) *Soybean Genet. News*. 17:43-48), a close relative of *G. max* (Hymowitz, T., "On the domestication of the soybean," (1970) *Econ. Bot*. 24:408-421), and other wild relatives (Zhuang, B. et al., "A study on resistance to soybean mosaic virus and *Aphis glycines* of perennial wild soybean," (1996) *Soybean Genet Newsl*. 23:66-69). There are no reports of resistance in *G. max*. A report from Indonesia indicated that there was no resistance in a test of 201 soybean cultivars and breeding lines (Sama, S. et al. (1974) Research Reports 1968-1974, p. 171-172. In Varietal screening for resistance to the aphid, *Aphis glycines*, in soybean. Agricultural Cooperation, Indonesia, the Netherlands).

There are numerous examples of the discovery and use of resistance genes to control aphids in crops other than soybean. Examples include Russian wheat aphid (Du Toit, F. (1987), "Resistance in wheat (*Triticum aestivum*) to *Diuraphis noxia* (Homoptera: Aphididae)," *Cereal Res. Commun*. 15:175-179; wheat greenbug (Tyler, J. M., et al. (1985), "Biotype E greenbug resistance in wheat streak mosaic virus-resistant wheat germplasm lines," Crop Science 25:686-688), potato aphid on tomato (Kaloshian, I., et al. (1997), "The impact of Meu-1-mediated resistance in tomato on longevity, fecundity and behavior of the potato aphid," *Macrosiphum euphorbiae*," *Entomol. Exp. Appl*. 83:181-187), and cotton-melon aphid on melon (Klinger, J. et al. (2001), "Mapping of cotton-melon aphid resistance in melon," *J. Am. Soc. Hortic. Ci*. 136:56-63)

A number of soybean markers have been mapped and linkage groups created, as described in Cregan, P. B., et al., "An Integrated Genetic Linkage Map of the Soybean Genome" (1999) Crop Science 39:1464-1490.

All publications referred to herein are incorporated herein by reference to the extent not inconsistent herewith.

Methods and molecular tools are needed to allow breeding of *A. glycines* resistance into high-yielding *G. max* soybean varieties.

SUMMARY OF THE INVENTION

A novel method is provided for determining the presence or absence in a soybean germplasm of a gene for resistance to the soybean aphid, *Aphis glycines*. The aphid resistance trait has been found to be closely linked to a number of molecular markers that map to linkage group M. Genes found on soybean linkage group M conferring the resistance trait are designated Rag11. The Rag1 gene was originally discovered in the resistance sources Dowling (PI548663) and Jackson (PI548657). ("PI" stands for "plant introductions" and these PI numbers refer to USDA depository accession numbers.) The trait of resistance to *Aphis glycines* is also found in other varieties as described hereafter.

In accordance with the present invention, the gene for resistance to *Aphis glycines* (the RAG gene) co-segregates with molecular markers with which it is linked on linkage group M, most preferably, Satt435, Satt463, Satt245, and DOP_H14. The Rag1 gene found on Dowling and Jackson has been found to map to a locus that lies between the markers Satt435 and Satt463. Other markers of linkage group M may also be used to identify the presence or absence of the gene. Preferably flanking markers are used for identifying the presence of a RAG gene or for marker-assisted breeding. Most preferably, the markers used map within about 20 cM, and more preferably within about 10 cM of a RAG locus (which contains the Rag1 gene), or within about 20 cM and more preferably within about 10 cM of Satt435 or Satt463.

The information disclosed herein regarding RAG loci is used to aid in the selection of breeding plants, lines and populations containing *Aphis glycines* resistance for use in introgression of this trait into elite soybean germplasm, or germplasm of proven genetic superiority suitable for variety release.

Also provided is a method for introgressing a soybean *Aphis glycines* resistance gene into non-resistant soybean germplasm or less resistant soybean germplasm. According to the method, nucleic acid markers linked to a RAG gene are used to select soybean plants containing a RAG locus. Plants so selected have a high probability of expressing the trait *Aphis glycines* resistance. Plants so selected can be used in a soybean breeding program. Through the process of introgression, the RAG locus is introduced from plants identified using marker-assisted selection to other plants. According to the method, agronomically desirable plants and seeds can be produced containing the RAG locus from germplasm containing a RAG gene.

Particular examples of sources of Rag1 resistance to *A. glycines* are the following G. max varieties: Dowling (PI548663) and its grandparent CNS (PI548445), Jackson (PI548657), and its parent Palmetto (PI548480). PI071506 is also a source of *A. glycines* resistance.

Other sources of *A. glycines* resistance are disclosed below.

Also provided herein is a method for producing an inbred soybean plant adapted for conferring, in hybrid combination, *Aphis glycines* resistance. First, donor soybean plants for a parental line containing a RAG gene are selected. According to the method, selection can be accomplished via nucleic acid marker-associated selection as explained herein. Selected plant material may represent, among others, an inbred line, a hybrid, a heterogeneous population of soybean plants, or simply an individual plant. According to techniques well known in the art of plant breeding, this donor parental line is crossed with a second parental line. Preferably, the second parental line is high yielding. This cross produces a segregating plant population composed of genetically heterogeneous plants. Plants of the segregating plant population are screened for the RAG locus. Those plants having the RAG locus are selected for further breeding until a line is obtained that is homozygous for resistance to *Aphis glycines* at the RAG locus. This further breeding may include, among other techniques, additional crosses with other lines, hybrids, backcrossing, or self-crossing. The result is an inbred line of soybean plants that are resistant to *Aphis glycines* and also have other desirable traits from one or more other inbred lines.

Soybean plants, seeds, tissue cultures, variants and mutants having *Aphis glycines* resistance produced by the foregoing methods are also provided in this invention.

DETAILED DESCRIPTION

Figure 1A:
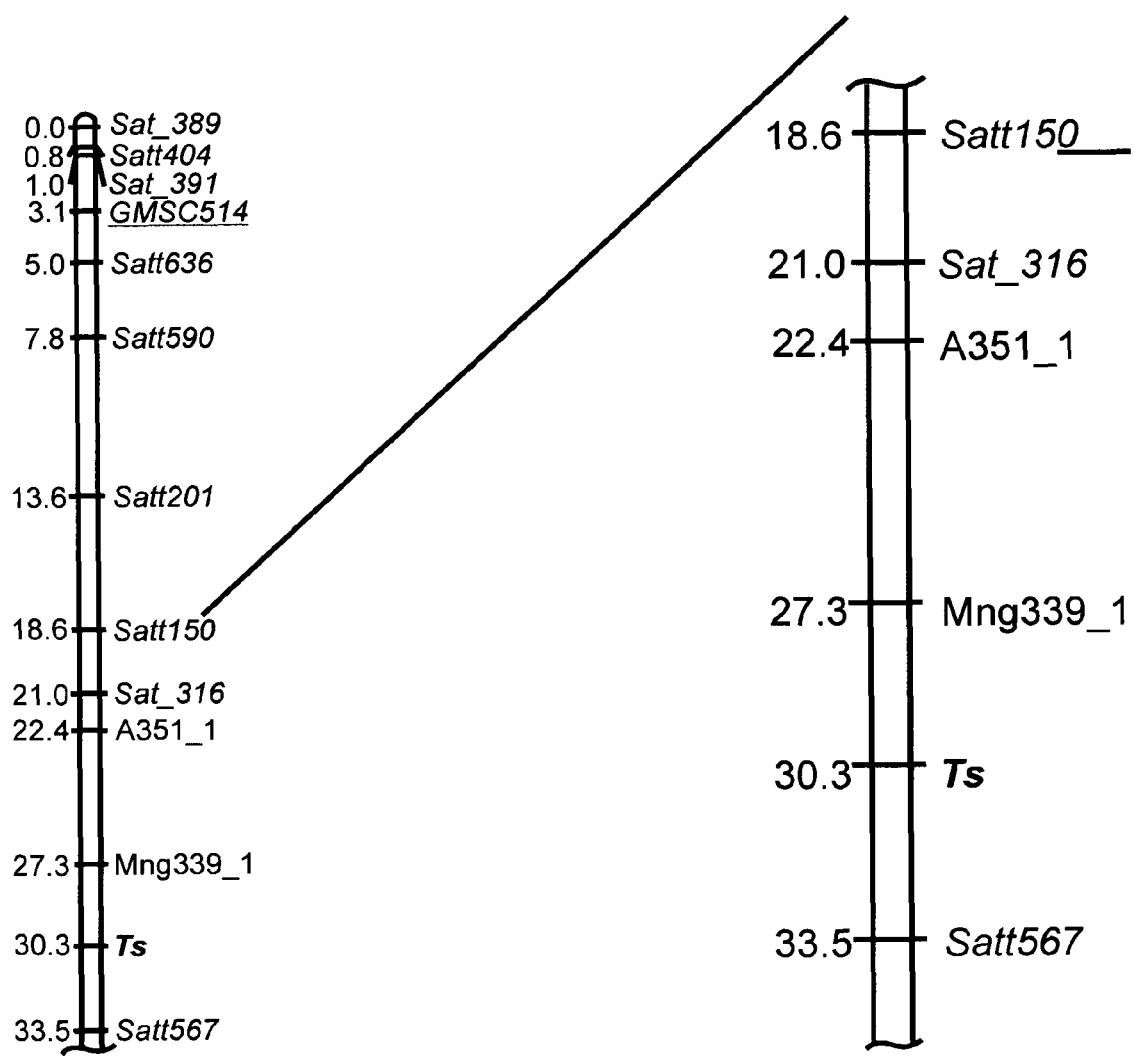
FIG. 1 shows a published soybean genetic linkage M composite map and anchored markers, in which SSR markers used to create the linkage map with the RAG gene indicated by horizontal lines. The map has been broken into four consecutive vertical sections, FIG. 1A through FIG. 1D.
Figure 1B:
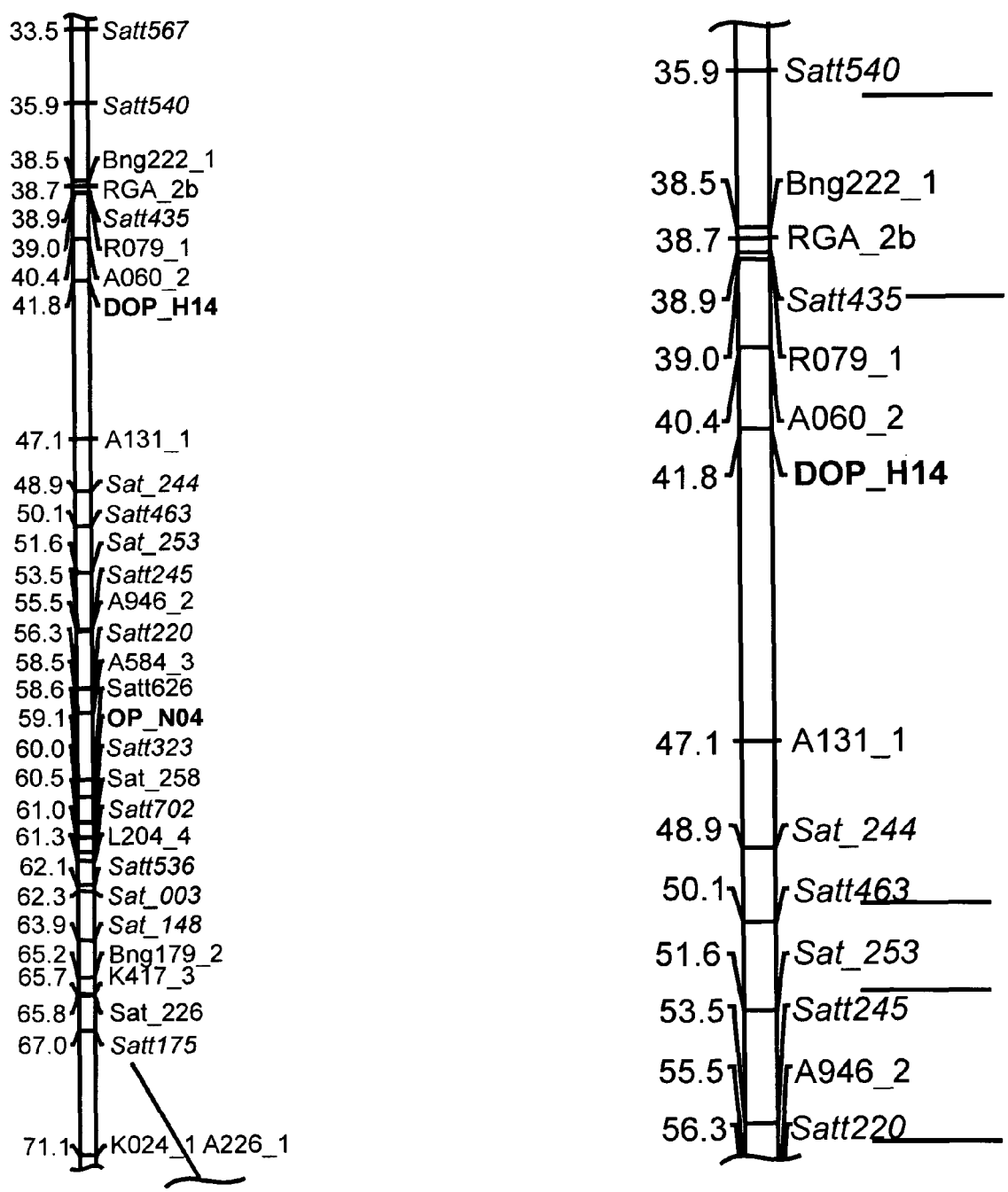
Figure 1C:
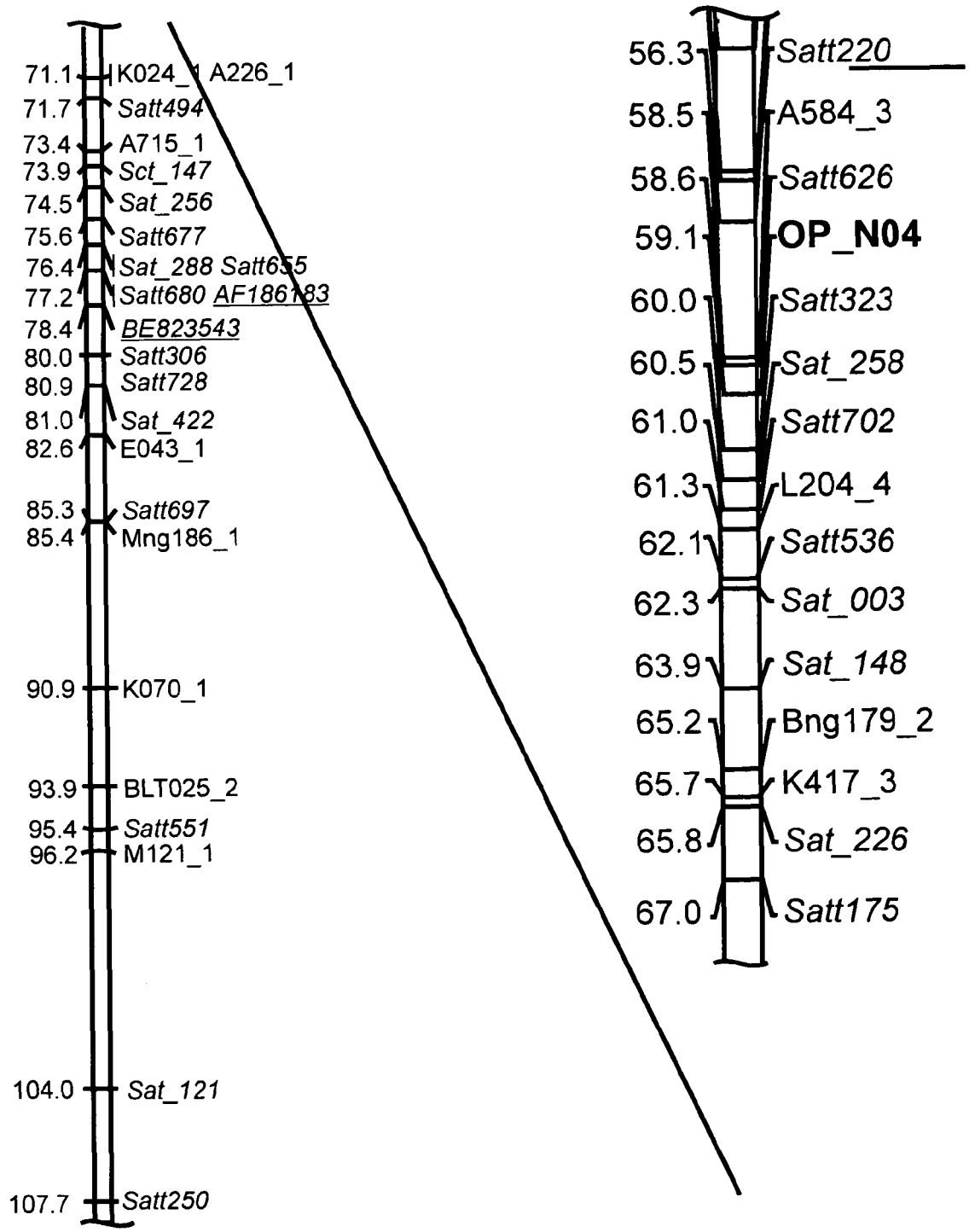
Figure 1D:
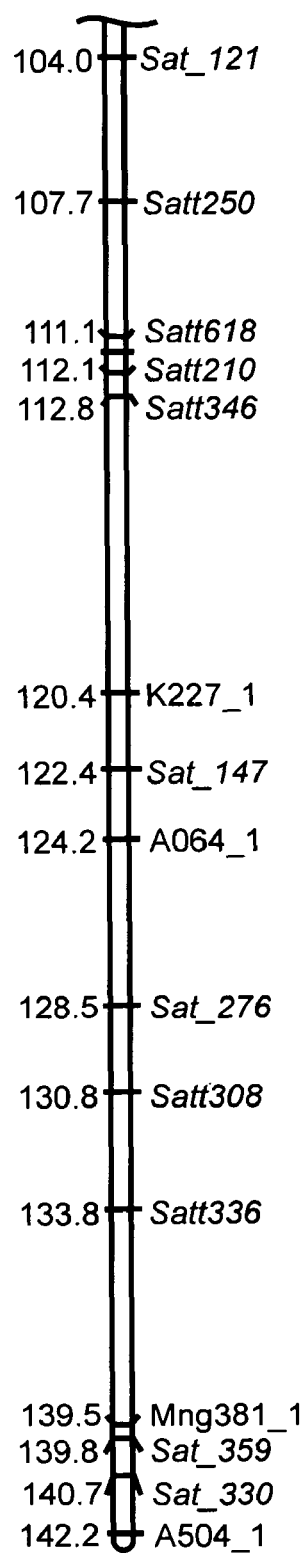

"Allele" is any of one or more alternative forms of a gene, all of which alleles relate to one trait or characteristic. In a diploid cell or organism, the two alleles of a given gene occupy corresponding loci on a pair of homologous chromosomes. The RAG genes in Dowling and Jackson may be allelic to each other.

"Backcrossing" is a process through which a breeder repeatedly crosses hybrid progeny back to one of the parents (recurrent parent), for example, a first generation hybrid $F_1$ with one of the parental genotypes of the $F_1$ hybrid.

"Cultivar" and "variety" are used synonymously and mean a group of plants within a species (e.g., *Glycine max*) that share certain genetic traits that separate them from the typical form and from other possible varieties within that species. Soybean cultivars are inbred lines produced after several generations of self-pollination. Individuals within a soybean cultivar are homogeneous, nearly genetically identical, with most loci in the homozygous state.

"Gene" means a specific sequence of nucleotides in DNA that is located in the germplasm, usually on a chromosome, and that is the functional unit of inheritance controlling the transmission and expression of one or more traits by specifying the structure of a particular polypeptide or controlling the function of other genetic material. In the present instance, RAG genes for resistance to *Aphis glycines* (RAG) have been found on RAG loci flanked by markers Satt435 and Satt463. The RAG gene is referred to as Rag1 when derived from or identical to the Dowling variety and when derived from or identical to the Jackson variety. RAG genes may be isolated by one skilled in the art without undue experiments by means known to the art including PCR cloning utilizing the adjacent Satt435 and Satt463 primer sequences, or primer sequences from other markers flanking the gene as described herein, by positional cloning using BACs (bacterial artificial chromosomes), or other methods. See, e.g., Wu, et al., "A BAC and BIBAC-based Physical Map of the Soybean Genome" (2004) Genome Res. Feb; 14(2):319-26, which describes the use of BACs in mapping the soybean genome. Contiguous BACs that have been found to be anchored to Satt435 and in which the Rag1 gene may be found include B03124⁻, B52J11*, B431224⁻, H57B23, H03O08, B36M08*, H62M17, H75H01, and E71J17. Information on these contiguous BACs is known to the art. Certain information is publicly available at the National Center for Biotechnology Information (NCBI) and GenBank web sites. The end sequence for H03O08 is set forth below:

single sequence repeats (SSRs). RFLP markers occur because any sequence change in DNA, including a single base change, insertion, deletion or inversion, can result in loss (or gain) of a restriction endonuclease recognition site. The size and number of fragments generated by one such enzyme is therefore altered. A probe that hybridizes specifically to DNA in the region of such an alteration can be used to rapidly and specifically identify a region of DNA that displays allelic variation between two plant varieties. SSR markers occur where a short sequence displays allelic variation in the number of repeats of that sequence. Sequences flanking the repeated sequence can serve as polymerase chain reaction (PCR) primers. Depending on the number of repeats at a given allele of

```
                                                         [SEQ ID NO: 1]
H03O08:
AAGCTTCTAT CAAGTGGTAA TCAGAGCACA AGATCTTCAA GTAGGTGATC

CTTAAACCTC CATTAATTTT TTGCTTTACC TTCTCTTCTA TTGTTGTTTC

TTCATTTTTC TCCATCTATC TCCTCACATG TCTTGTGCTA AATGTTTTTA

ACATCATTCT TTAGAGTTTC CACCGATTAA ACTTGCTATA GAAGCTAGAT

TTGATTTTCT ATGGTTCAAA TTTCTTGTTC TTGTTCTTGA TCCATGAATT

GTGTTGAGTT TAGGTTCCTT TGAGTTTTGT CTTGTTATTT TTTGTGGCTG

AAACCTAAAC CATAAAATTC TTACAAAAAT ATTAAAGTAG AGGAAAACCT

CAAAAATCTA GAGTGACTTG TTCACCTATT ATAGTTTTGT CATAGAAGTC

ATGTCTAGTC ATGAAACTTG TCACATAAGA TTTCTTATGT TGTGCTGAAT

TTTATTTTCT TGTTTCTTTG TCTAACTCAT TTGTTCATGA GTGTATGAAG

TTATTTTAGC CTATTATTTG ATTGGAGTCA AATCTTTCAT GTTAATTAGT

CCTTAACATG TTCATGCAAA ATTCTTAGAG AGTCTTTGAT TGTGAACCTT

TTCTTGAACT TTTAGGTTTC CTTATGATTG TGTCTATTGT GAATTTAAGT

TTTGGTGATT GAATTGCTGG TTGAAATGTT GATCCTAAGT GAATATTGAA

CTCCTAAAAC TGTGGTAAAC AATCCTAGTG AGTTCAACAT ACATAGGAAG

GTTGAAAGTA AGCCCAAGGC AATCAATATA GCATGCTTAA AAAAAAAATC

GCTGGTGCTG GCAGCTTGGA CATACAAACT TGTAAAAATT ACTGAAAATT

GGTTACTTCG AATTTTGAAC TGAATTTTTA CTTAATTTGC TAGA
```

"Germplasm" means the genetic material with its specific molecular and chemical makeup that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

"Hybrid plant" means a plant offspring produced by crossing two genetically dissimilar parent plants.

"Inbred plant" means a member of an inbred plant strain that has been highly inbred so that all members of the strain are nearly genetically identical.

"Introgression" means the entry or introduction by hybridization of a gene or trait locus from the genome of one plant into the genome of another plant that lacks such gene or trait locus.

"Molecular marker" is a term used to denote a nucleic acid or amino acid sequence that is sufficiently unique to characterize a specific locus on the genome. Examples include restriction fragment length polymorphisms (RFLPs) and the locus, the length of the DNA segment generated by PCR will be different in different alleles. The differences in PCR-generated fragment size can be detected by gel electrophoresis. Other types of molecular markers are known. All are used to define a specific locus on the soybean genome. Large numbers of these have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming, requiring growing up of plants to a stage where the trait can be expressed.

Another type of molecular marker is the random amplified polymorphic DNA (RAPD) marker. Chance pairs of sites complementary to single octa- or decanucleotides may exist in the correct orientation and close enough to one another for PCR amplification. With some randomly chosen decanucleotides no sequences are amplified. With others, the same length products are generated from DNAs of different individuals. With still others, patterns of bands are not the same for every individual in a population. The variable bands are commonly called random amplified polymorphic DNA (RAPD) bands.

Another type of molecular marker is the target region amplification polymorphism (TRAP) marker. The TRAP technique employs one fixed primer of known sequence in combination with a random primer to amplify genomic fragments.

A further type of molecular marker is the single nucleotide polymorphism (SNP) marker, in which DNA sequence variations that occur when a single nucleotide (A, T, C, or G) in the genome sequence is altered are mapped to sites on the soybean genome.

Other molecular markers known to the art, as well as phenotypic traits may be used as markers in the methods of this invention.

"Linkage" is defined by classical genetics to describe the relationship of traits that co-segregate through a number of generations of crosses. Genetic recombination occurs with an assumed random frequency over the entire genome. Genetic maps are constructed by measuring the frequency of recombination between pairs of traits or markers. The closer the traits or markers lie to each other on the chromosome, the lower the frequency of recombination, the greater the degree of linkage. Traits or markers are considered herein to be linked if they generally co-segregate. A 1/100 probability of recombination per generation is defined as a map distance of 1.0 centiMorgan (1.0 cM). Preferably markers useful for screening for the presence of *Aphis glycines* resistance (RAG) map to within 20 cM of the trait, and more preferably within 10 cM of the trait.

A second marker that maps to within 20 cM of a first marker that co-segregates with the RAG trait and generally co-segregates with the RAG trait is considered equivalent to the first marker. Any marker that maps within 20 cM and more preferably 10 cM of the RAG trait belongs to the class of preferred markers for use in screening and selection of soybean germplasm having the RAG *Aphis glycines* resistance trait. A number of markers are known to the art to belong to linkage group M on which the RAG trait is found. A number of markers are proprietary markers known only to certain of those skilled in the art of soybean plant breeding. A proprietary marker mapping within 20 cM, and preferably within 10 cM, of any publicly known marker specified herein is considered equivalent to that publicly-known marker.

"Linkage group" refers to traits or markers that generally co-segregate. A linkage group generally corresponds to a chromosomal region containing genetic material that encodes the traits or markers.

"Locus" means a chromosomal region where a polymorphic nucleic acid or trait determinant or gene is located.

"Polymorphism" means a change or difference between two related nucleic acids. A "nucleotide polymorphism" refers to a nucleotide that is different in one sequence when compared to a related sequence when the two nucleic acids are aligned for maximal correspondence. A "genetic nucleotide polymorphism" refers to a nucleotide that is different in one sequence when compared to a related sequence when the two nucleic acids are aligned for maximal correspondence, where the two nucleic acids are genetically related, i.e., homologous, for example, where the nucleic acids are isolated from different strains of a soybean plant, or from different alleles of a single strain, or the like.

"Marker assisted selection" means the process of selecting a desired trait or desired traits in a plant or plants by detecting one or more nucleic acids from the plant, where the nucleic acid is linked to the desired trait.

"Plant" means plant cells, plant protoplast, plant cell or tissue culture from which soybean plants can be regenerated, plant calli, plant clumps and plant cells that are intact in plants or parts of plants, such as seeds, pods, flowers, cotyledons, leaves, stems, buds, roots, root tips and the like.

"Probe" means an oligonucleotide or short fragment of DNA designed to be sufficiently complementary to a sequence in a denatured nucleic acid to be probed and to be bound under selected stringency conditions.

"Rag1-derived resistance" means resistance in a soybean germplasm to *Aphis glycines* that is provided by the heterozygous or homozygous expression of the Rag1 gene within the RAG locus mapped between the SSR markers Satt435 and Satt463. "RAG-derived resistance" means *Aphis glycines* resistance conferred by a RAG gene on a RAG locus, the use of which is enabled by the disclosure herein.

"RAG phenotype" means resistance to *Aphis glycines* by soybean germplasm, as demonstrated by resistance to *Aphis glycines* after inoculation with same according to the methods described herein.

"RAG soybean plant" means a plant having resistance to *Aphis glycines* that is derived from the presence and expression of at least one RAG gene, or that is shown to have a RAG gene at the RAG locus described herein.

"Self-crossing or self-pollination" is a process through which a breeder crosses hybrid progeny with itself, for example, a second generation hybrid $F_2$ with itself to yield progeny designated $F_{2:3}$.

As used herein, the terms "segregate," "segregants," "co-segregate," "hybrid," "crossing," and "selfing" refer to their conventional meanings as understood in the art (see, for instance, Briggs, F. N. and Knowles, P. F. and, *Introduction to Plant Breeding* (Reinhold Publication Corp., New. York, N.Y., 1967).

Markers that "flank" the RAG genes are markers that occur one to either side of a RAG gene. Flanking marker DNA sequences may be part of the gene or may be separate from the gene.

The method for determining the presence or absence of a RAG gene, which confers resistance to the soybean aphid *Aphis glycines* in soybean germplasm, comprises analyzing genomic DNA from a soybean germplasm for the presence of at least one molecular marker, wherein at least one molecular marker is linked to the RAG trait locus, and wherein the RAG trait locus preferably maps to soybean major linkage group M and is associated with resistance to the soybean aphid *Aphis glycines*. The term "is associated with" in this context means that the RAG locus containing the RAG gene has been found, using marker-assisted analysis, to be present in soybean plants showing resistance to *Aphis glycines* in live aphid bioassays as described herein.

The Rag1 gene occurs in the following varieties CNS (PI548445), Dowling (PI548663), Jackson (PI548657), and Palmetto (PI548480), among others.

Other sources of *A. glycines* resistance include the *G. max* varieties: Moyashimame (PI87059), Sato (PI548409), Showa No. 1-4 (PI88508), Sugao Zarai (PI200538), T26OH (PI548237), PI71506, and PI230977 of *G. max*, and G3, JS1, L4, S12 Taichung 38 (PI518282 and Taichung 37 (PI518281), of *G. soja*, and progeny of these varieties.

Table 1 lists *Glycine max.* varieties that are sources of resistance to the soybean aphid. Progeny of these varieties also containing a RAG gene are also sources of resistance to the soybean aphid.

TABLE 1

SOURCES OF RESISTANCE TO SOYBEAN APHID

| PI # | Name |
|---|---|
| 71506 | |
| 87059 | Moyashimame |
| 88508 | Showa No. 1-4 |
| 200538 | Sugao Zarai |
| 230977 | |
| 417084A | Kumaji 1 |
| 437696 | San-haj-hun-mao-huan-dou |
| 499955 | |
| 507298 | Sokoshin (Kamigoumura) |
| 508294 | |
| 518726 | Bao jiao huang |
| 548237 | T260H |
| 548409 | Sato |
| 548445 | CNS |
| 548480 | Palmetto |
| 548657 | Jackson |
| 548663 | Dowling |
| 567391 | Jiang se huang dou |
| 567541B | |
| 567543C | |
| 567597C | |
| 567598B | |
| 587552 | Nan jing da ping ding huang yi 1 |
| 587553A | |
| 587559B | (Dan tu he shang tou jia) |
| 587617 | Jin tan qing zi |
| 587656 | Huang dou |
| 587663 | Zhong chun huang dou |
| 587664B | (Shan zi bai) |
| 587666 | Er dao zao |
| 587668A | Hui mei dou |
| 587669 | Zan zi bai |
| 587674A | Ba yue bai |
| 587677 | Xiao li huang |
| 587682A | Da li huang 1 |
| 587684A | Ai jiao huang |
| 587685 | Da li huang 2 |
| 587686A | Xi li huang 1 |
| 587687A | Xiao li dou 1 |
| 587693 | Yu shan dou |
| 587700A | Da qing dou |
| 587702 | Qing pi dou |
| 587717 | Xiang yang ba yue zha |
| 587723A | Ying shan ji mu wo |
| 587732 | Ying shan ji mu wo |
| 587759 | Song zi ba yue cha |
| 587763 | Jing huang 36 |
| 587775 | Tong shan si ji dou |
| 587800 | Ying shan da li huang |
| 587816 | Bai mao dou |
| 587824 | Ying shan qing pi cao |
| 587840 | Du wo dou |
| 587844C | (Tong cheng hei se dou) |
| 587861 | Da qing dou |
| 587863B | (Liu yue bai) |
| 587870 | Huang pi dou |
| 587871 | Bao mao dou |
| 587873 | Feng wo dou |
| 587876 | Xi mao dou |
| 587877A | Jiu yue zao |
| 587891A | Qi yue ba |
| 587897 | Qing pi dou |
| 587899 | Ba yue bai |
| 587905 | Xiao huang dou |
| 587972 | Chang zi dou |
| 588000 | Shi yue huang |
| 588040 | Shan xing dou |
| 594421 | Da du huang dou |
| 594425 | Xiao cao huang dou |
| 594426A | Tie jiao huang |

TABLE 1-continued

SOURCES OF RESISTANCE TO SOYBEAN APHID

| PI # | Name |
|---|---|
| 594426B | (Tie jiao huang) |
| 594427A | Ba yue mang |
| 594431 | Chang pu qing dou |
| 594499 | Luo ma aluo |
| 594503 | Mu gu hei chi huang dou |
| 594514 | Hua lian dou |
| 594554 | Huang pi tian dou |
| 594557B | (Lao shu dou) |
| 594560B | (Xia shui huang) |
| 594573 | Lu pi dou |
| 594586A | |
| 594592 | Shi yue xiao huang dou |
| 594595 | Ba yue da huang dou (jia) |
| 594666B | (Liu yue mang -5) |
| 594703 | Qing pi dou -1 |
| 594707 | Da hei dou |
| 594711B | (Qing huang za dou -3) |
| 594751A | Long zhou dong feng dou |
| 594822 | Xi huang dou |
| 594864 | Yang yan dou |
| 594868 | Huang dou |
| 594879 | Huo shao dou |
| 603521 | |
| 603530A | |
| 603538A | |
| 603640 | |
| 603644 | |
| 603650 | |
| 605771 | |
| 605823 | |
| 605855 | |
| 605902 | |

The following *G. soja* varieties are also sources of *A. glycines* resistance: PI441008, PI573059, and PI573071, and progeny of these varieties.

Any one of the foregoing varieties or their progeny bearing a RAG gene may be used in the methods of this invention, and any combination thereof is considered to be a class of varieties useful in the methods of this invention.

Preferably a marker used to determine the presence or absence of a RAG gene is Satt435, Satt463, Satt245, S04309, S01623, or DOP_H14, or a marker that maps to within at least about 10 to about 20 cM of any of said markers.

Any marker assigned to soybean linkage group M may be useful for this purpose. Exemplary markers of linkage group M include Sat_389, Satt404, Sat_391, GMSC514, Satt636, Satt590, GM177, GM175, Satt201, Satt150, Sat_316, A351_1, Mng339_1, Ts, S01256, S02020, Satt567, Satt540, Bng222_1, RGA_2b, RGA5b, GM260, S04309, Satt435, R079_1, A060-2, DOP_H14, GM260, A131_1, Sat_244, S01623, Satt463, Sat_253, S03544, Satt245, GM284, A946_2, GM256, GMS057, Satt220, A584_3, Satt626, OP_N04, Satt323, Sat_258, Satt702, L204_4, GMS003b, Satt536, Sat_003, OM11_1100, Sat_148, Bng179_2, K417_3, Sat_226, Satt175, K024_1, A226_1, GM230, ACCAGC315, Satt494, B157_2, A715_1, Sat_147, Sat_256, Satt677, Sat_288, Satt655, Satt680, AF186183, BE823543, Satt306, A458_4, Satt728, Sat_422, E043_1, Satt697, Mng186_1, GM163, K070_1, AC_1, BLT025_2, Cr326_3, Satt551, M121_1, Satt551, Sat_131, Satt250, Satt618, Satt210, Satt346, K227_1, Sat_147, A064_1, GM141, GM209b, GM035a, A504_1, Sat_276, Satt308, Satt336, Mng381_1, Sat359, Sat_330, and A504.1.

Updated information regarding markers assigned to soybean linkage group M may be found on the USDA's Soybase website. Table 2 provides current information on the genbank location and allele size of markers useful in this invention. Table 3 provides upper and lower primer sequences.

TABLE 2

MARKERS

| Name | Type | GenBank gi # | cM Position in linkage group | GenBank Accession # | Allele Size in Williams |
|---|---|---|---|---|---|
| Sat_389 | SSR | 31044744 | 0.00 | CC453914 | |
| Satt404 | SSR | 14970089 | 0.84 | BH126586 | 181 |
| Sat_391 | SSR | 31044746 | 1.02 | CC453916 | |
| GMSC514 | SSR | 18745 | 3.05 | X56139 | 160 |
| Satt636 | SSR | 31044825 | 5.00 | CC453995 | 172 |
| Satt590 | SSR | 14970259 | 7.84 | BH126756 | 318 |
| Satt201 | SSR | 14969911 | 13.56 | BH126408 | 282 |
| Satt150 | SSR | 14969865 | 18.58 | BH126362 | 201 |
| Sat_316 | SSR | 31044677 | 21.00 | CC453847 | 298 |
| A351_1 | RFLP | | 22.394 | | |
| Mng339_1 | RFLP | | 27.325 | | |
| Ts | UNKNOWN | | 30.251 | | |
| Satt567 | SSR | 14970236 | 33.493 | BH126733 | 110 |
| Satt540 | SSR | 14970211 | 35.85 | BH126708 | 152 |
| Bng222_1 | RFLP | | 38.504 | | |
| RGA2B | RFLP | | 38.679 | | |
| Satt435 | SSR | 14970116 | 38.94 | BH126613 | 286 |
| R079_1 | RFLP | | 40.354 | | |
| A0560_2 | RFLP | | 40.354 | | |
| DOP-H14 | RAPD | | 41.836 | 41.836 | |
| A131_1 | RFLP | | 47.12 | | |
| Sat_244 | SSR | 31044612 | 48.86 | CC453782 | 224 |
| Satt463 | SSR | 14970139 | 50.10 | BH126636 | 226 |
| Sat_253 | SSR | 31044619 | 51.60 | CC453789 | 275 |
| Satt245 | SSR | 14969948 | 53.54 | BH126445 | 211 |
| A946_2 | RFLP | | 55.492 | | |
| Satt220 | SSR | 14969926 | 56.29 | BH126423 | 245 |
| A584.3 | RFLP | | 58.501 | | |
| Satt626 | SSR | 31044818 | 58.60 | CC453988 | 238 |
| OP_N04 | RAPD | | 59.11 | | |
| Satt323 | SSR | 14970017 | 60.05 | BH126514 | 156 |
| Sat_258 | SSR | 31044623 | 60.47 | CC453793 | 193 |
| Satt702 | SSR | 31044881 | 61.04 | CC454051 | |
| L204_4 | RFLP | | 61.26 | | |
| Satt536 | SSR | 14970207 | 62.14 | BH126704 | 162 |
| Sat_003 | SSR | 14969756 | 62.31 | BH126253 | 161 |
| Sat_148 | SSR | 31044530 | 63.93 | CC453700 | 162 |
| Bng179_2 | RFLP | | 65.213 | | |
| K417_3 | RFLP | | 65.694 | | |
| Sat_226 | SSR | 31044595 | 65.79 | CC453765 | 212 |
| Satt175 | SSR | 14969887 | 66.99 | BH126384 | 163 |
| K024_1 | RFLP | | 71.05 | | |
| A226_1 | RFLP | | 71.094 | | |
| Satt494 | SSR | 14970168 | 71.71 | BH126665 | 218 |
| A715_1 | RFLP | | 73.373 | | |
| Sct_147 | SSR | 14970282 | 73.88 | BH126779 | |
| Sat_256 | SSR | 31044622 | 74.53 | CC453792 | 253 |
| Satt677 | SSR | 31044860 | 75.57 | CC454030 | 157 |
| Sat_288 | SSR | 31044651 | 76.41 | CC453821 | 215 |
| Satt655 | SSR | 31044840 | 76.41 | CC454010 | 287 |
| Satt680 | SSR | 31044863 | 77.19 | CC454033 | 304 |
| AF186183 | SSR | 6671123 | 77.24 | AF186183 | |
| BE823543 | SSR | 10255728 | 78.38 | BE823543 | |
| Satt306 | SSR | 14970000 | 80.02 | BH126497 | 212 |
| Satt728 | SSR | 31044900 | 80.90 | CC454070 | |
| Sat_422 | SSR | 31044776 | 80.97 | CC453946 | |
| E043_1 | RFLP | | 82.645 | | |
| Satt697 | SSR | 31044876 | 85.35 | CC454046 | 302 |
| Mng186_1 | RFLP | | 85.433 | | |
| K070_1 | RFLP | | 90.921 | | |
| BLT025_2 | RFLP | | 93.941 | | |
| Satt551 | SSR | 14970221 | 95.45 | BH126718 | 238 |
| M121_1 | RFLP | | 96.222 | | |
| Sat_121 | SSR | 14969794 | 103.98 | BH126291 | 189 |
| Satt250 | SSR | 14969951 | 107.70 | BH126448 | 202 |
| Satt618 | SSR | 31044812 | 111.06 | CC453982 | 117 |
| Satt210 | SSR | 14969919 | 112.08 | BH126416 | 260 |
| Satt346 | SSR | 14970039 | 112.79 | BH126536 | 208 |
| K227_1 | RFLP | | 120.373 | | |
| Sat_147 | SSR | 31044529 | 122.37 | CC453699 | 265 |
| A064_1 | RFLP | | 124.212 | | |
| Sat_276 | SSR | 31044640 | 128.48 | CC453810 | 271 |
| Satt308 | SSR | 14970002 | 130.76 | BH126499 | 170 |
| Satt336 | SSR | 14970030 | 133.83 | BH126527 | 170 |
| Mng381_1 | RFLP | | 139.46 | | |
| Sat_359 | SSR | 31044715 | 139.81 | CC453885 | |
| Sat_330 | SSR | 31044687 | 140.69 | CC453857 | 265 |
| A504_1 | RFLP | | 142.184 | | |

TABLE 3

MARKER SEQUENCES

| Name | Upper primer sequence (5' → 3') | Lower primer sequence (5' → 3') |
|---|---|---|
| Sat_389 | GCGGGTAGCCATATTCATATATTGCTG [SEQ ID NO: 2] | GCGAAGGCTTATAAGGAGATACGATTTA [SEQ ID NO: 3] |
| Satt404 | TCATCCGCCATTGATTTT [SEQ ID NO: 4] | GCCCGGAACATACAAAAT [SEQ ID NO: 5] |
| Sat_391 | GCGTAGGCATCGGTCAATATTTT [SEQ ID NO: 6] | GCGTTAGCGAGTGGATCAAGATCA [SEQ ID NO: 7] |
| GMSC514 | TACCTTTCTTGTGAGTCGTA [SEQ ID NO: 8] | TATTGAGATGGATATTGTAGATC [SEQ ID NO: 9] |
| Satt636 | GTCATGACTCATGAGTCACGTAAT [SEQ ID NO: 10] | CCCAAGACCCCCATTTTTATGTCT [SEQ ID NO: 11] |
| Satt590 | GCGCGCATTTTTTAAGTTAATGTTCT [SEQ ID NO: 12] | GCGCGAGTTAGCGAATTATTTGTC [SEQ ID NO: 13] |
| Satt201 | GCGTTGATACTTTCCTAAGACAAT [SEQ ID NO: 14] | GGGAGAGAAGGCAATCTAA [SEQ ID NO: 15] |

TABLE 3-continued

MARKER SEQUENCES

| Name | Upper primer sequence (5' → 3') | | Lower primer sequence (5' → 3') | |
|---|---|---|---|---|
| Satt150 | AAGCTTGAGGTTATTCGAAAAATGAC | [SEQ ID NO: 16] | TGCCATCAGGTTGTGTAAGTGT | [SEQ ID NO: 17] |
| Sat_316 | GCGCAACGTCTAAAGCACAAGGATT | [SEQ ID NO: 18] | GCGCGACTACGTTACAGTTCCAA | [SEQ ID NO: 19] |
| Satt567 | GGCTAACCCGCTCTATGT | [SEQ ID NO: 20] | GGGCCATGCACCTGCTACT | [SEQ ID NO: 21] |
| Satt540 | CTGGCGAATCAAGCTTTGTAAC | [SEQ ID NO: 22] | CCGTGATTGCGAAGAGGATATT | [SEQ ID NO: 23] |
| Satt435 | GCGGTGAAACGGCTCTCTTTGATAGTGA | [SEQ ID NO: 24] | GCGTTGGATTAATTAATTAAATTATTTT | [SEQ ID NO: 25] |
| Sat_244 | GCGTCAACCGGTGAAAAAACCTA | [SEQ ID NO: 26] | GCGTGGCTGGCAGTAGTCTATATCA | [SEQ ID NO: 27] |
| Satt463 | TTGGATCTCATATTCAAACTTTCAAG | [SEQ ID NO: 28] | CTGCAAATTTGATGCACATGTGTCTA | [SEQ ID NO: 29] |
| Sat_253 | GCGATTGGTTGGGTGTTTAATTTTAAGAT | [SEQ ID NO: 30] | GCGTGTTGATGGTATAAAGATCGCTACTCT | [SEQ ID NO: 31] |
| Satt245 | AACGGGAGTAGGACATTTTATT | [SEQ ID NO: 32] | GCGCCTCCTGAATTTCAAGAATGAAGA | [SEQ ID NO: 33] |
| Satt220 | GAGGAGGATCCCAAGGTAATAAT | [SEQ ID NO: 34] | GCGCATGGAGAAAAGAAGAG | [SEQ ID NO: 35] |
| Satt626 | GCGGATGGAGACGGGGGCACGGACGA | [SEQ ID NO: 36] | GCGCATAGCTAATTTTATATCAATTAT | [SEQ ID NO: 37] |
| Satt323 | GCGGTCGTCCTATCTAATGAAGAG | [SEQ ID NO: 38] | TGTGCGTTTAAATTGCAGCTAAAT | [SEQ ID NO: 39] |
| Sat_258 | GCGCAATAGATAATCGAAAAACATACAAGA | [SEQ ID NO: 40] | GCGGGGAAAGTGAAAACAAGATCAAATA | [SEQ ID NO: 41] |
| Satt702 | GCGGGGTTCTGTGGCTTCAAC | [SEQ ID NO: 42] | GCGCATTGGAATAACGTCAAA | [SEQ ID NO: 43] |
| Satt536 | GCGCCACAGAAATTCCTTTTTCTA | [SEQ ID NO: 44] | GCGCCATAAGGTGGTTACCAAAAGA | [SEQ ID NO: 45] |
| Sat_003 | TGATTTTTGGTGTAGAACTC | [SEQ ID NO: 46] | CAAATTGGTTAGCTTACTCCA | [SEQ ID NO: 47] |
| Sat_148 | GCGGAGTTTCCCCTAATTAGAT | [SEQ ID NO: 48] | GCGCAAGCTAGCTTCACCCAAAACTA | [SEQ ID NO: 49] |
| Sat_226 | GCGGAAACCCACCTATATGTGATCAAATG | [SEQ ID NO: 50] | GCGCAATTCCAGATGAAACAGAAGAAGGAT | [SEQ ID NO: 51] |
| Satt175 | GACCTCGCTCTCTGTTTCTCAT | [SEQ ID NO: 52] | GGTGACCACCCCTATTCCTTAT | [SEQ ID NO: 53] |
| Satt494 | GGCCGGTTCTCATTACAGGTCTCT | [SEQ ID NO: 54] | GGATTTCCATCTTGAATTTTATTA | [SEQ ID NO: 55] |
| Sct_147 | TCTCGACTCACGACTCA | [SEQ ID NO: 56] | CCAAGGTCTCTCAGAGG | [SEQ ID NO: 57] |
| Sat_256 | GCGCGGAAAATTATTTTACTTTTTCAAT | [SEQ ID NO: 58] | GCGCACGGATTGAGAGAAAGCAGAAAGA | [SEQ ID NO: 59] |
| Satt677 | CAACGACCAACTGACGAGACCT | [SEQ ID NO: 60] | GGGAATTCAACATGTGATGGTTTT | [SEQ ID NO: 61] |
| Sat_288 | GCGACAGACTGCAAGAATTGATGTAAATCT | [SEQ ID NO: 62] | GCGGGAAGGTAGGTAAAGAAATTCAAATGA | [SEQ ID NO: 63] |
| Satt655 | GAAGACCAAAACTTATTTCAGATC | [SEQ ID NO: 64] | ATTTTAAGCACCAGCAAAGACT | [SEQ ID NO: 65] |
| Satt680 | GCGGGATATCGTGAGCATAGTTTTAC | [SEQ ID NO: 66] | GCGGCCTGAATATTTTAGGTTTAGAGTT | [SEQ ID NO: 67] |

TABLE 3-continued

MARKER SEQUENCES

| Name | Upper primer sequence (5' → 3') | | Lower primer sequence (5' → 3') | |
|---|---|---|---|---|
| AF186183 | GCGTATTTTGGGGGATTTTGAACA | [SEQ ID NO: 68] | GCGTTTCTCTTCTTATTCTTTCTCT | [SEQ ID NO: 69] |
| BE823543 | GCGAAATGCCGAAAGAG | [SEQ ID NO: 70] | GCGGGGATAAGAAAAACAAT | [SEQ ID NO: 71] |
| Satt306 | GCGCTTAAGGACACGGATGTAAC | [SEQ ID NO: 72] | GCGTCTCTTTCGATTGTTCTATTAG | [SEQ ID NO: 73] |
| Satt728 | GCGTACCCCTATATGGATGTTTCTTCCT | [SEQ ID NO: 74] | GCGTATGCAGCAAACAAAAATATATAAT | [SEQ ID NO: 75] |
| Sat_422 | GCGTTTTCCTAATGAAGATTT | [SEQ ID NO: 76] | GCGTGTAATAGTGATGGATGTAA | [SEQ ID NO: 77] |
| Satt697 | GCGTGCTTTAAATGATTGATTGA | [SEQ ID NO: 78] | GCGTGCGAACATAACTAATACAT | [SEQ ID NO: 79] |
| Satt551 | GAATATCACGCGAGAATTTTAC | [SEQ ID NO: 80] | TATATGCGAACCCTCTTACAAT | [SEQ ID NO: 81] |
| Sat_121 | GACAAATGTAAAAAGTGACAGATAGAATGT | [SEQ ID NO: 82] | GTGTGGTGGTGGTACAGTTTTATACTAA | [SEQ ID NO: 83] |
| Satt250 | CGCCAGCTAGCTAGTCTCAT | [SEQ ID NO: 84] | AATTTGCTCCAGTGTTTTAAGTTT | [SEQ ID NO: 85] |
| Satt618 | GCGGTGATATTACCCCAAAAAAATGAA | [SEQ ID NO: 86] | GCGCTAGTTTCTAGTGGAAAGATGAGT | [SEQ ID NO: 87] |
| Satt210 | GCGAAAAACGTCAGGTCAATGACTGAAA | [SEQ ID NO: 88] | GCGGGGCTTAGATATAAAAAAAAAGATG | [SEQ ID NO: 89] |
| Satt346 | GGAGGGAGGAAAGTGTTGTGG | [SEQ ID NO: 90] | GCGCATGCTTTTCATAAGTTT | [SEQ ID NO: 91] |
| Sat_147 | GTGCGACGTCATGCCTTACTCAAT | [SEQ ID NO: 92] | GCGCTCCGTACACTTAAAAAAGAA | [SEQ ID NO: 93] |
| Sat_276 | GCGGAAACCCATCTAGAATATGAAAACA | [SEQ ID NO: 94] | GCGTTCTTCTCGAGGTGAGATACAATC | [SEQ ID NO: 95] |
| Satt308 | GCGTTAAGGTTGGCAGGGTGGAAGTG | [SEQ ID NO: 96] | GCGCAGCTTTATACAAAAATCAACAA | [SEQ ID NO: 97] |
| Satt336 | AATTGGAGTGGGTCACAC | [SEQ ID NO: 98] | TTCCCGGAAAGAAAGAAA | [SEQ ID NO: 99] |
| Sat_359 | GCGGGTCACGATTCTAGTCACTATAACTTCA | [SEQ ID NO: 100] | GCGCAACGTAAGAAATGTAAATACAATGGA | [SEQ ID NO: 101] |
| sat_330 | GCGTTAGGATTTAGGATGAGGATAGG | [SEQ ID NO: 102] | GCGCAAATCAGTTGAGCAATGACTTA | [SEQ ID NO: 103] |

The sequence of the RAPD marker DOP_H14 is: 5' to 3': ACCAGGTTGG [SEQ ID NO:104].

Table 4 provides information on additional SNP markers that are useful in practicing the present invention, showing their relative locations with respect to the markers described in Tables 2 and 3.

TABLE 4

SNP MARKERS

| Locus | SNP ID | BARC Seq. ID | Type | GenBank source seq. | Position in LG |
|---|---|---|---|---|---|
| S01256 | BARC-GM-01256 | 13845 | 3'mRNAsequence | AW348751 | 33.493 |
| S02020 | BARC-GM-02020 | 15945 | 3'mRNAsequence | AW349790 | 33.493 |
| Satt567 | | | | | 33.493 |
| Satt540 | | | | | 35.879 |

TABLE 4-continued

SNP MARKERS

| Locus | SNP ID | BARC Seq. ID | Type | GenBank source seq. | Position in LG |
|---|---|---|---|---|---|
| Bng222_1 | | | | | 38.528 |
| RGA_2b | | | | | 38.703 |
| S04309 | BARC-GM-04309 | 22289 | 3'mRNAsequence | AW351227 | 38.964 |
| Satt435 | | | | | 38.964 |
| R079_1 | | | | | 39.004 |
| A060_2 | | | | | 40.378 |
| DOP_H14 | | | | | 41.858 |
| A131_1 | | | | | 47.142 |
| Sat_244 | | | | | 48.876 |
| S01623 | BARC-GM-01623 | 14705 | 3'mRNAsequence | AW349229 | 50.117 |
| Satt463 | | | | | 50.117 |
| Sat_253 | | | | | 51.617 |
| S03544 | BARC-GM-03544 | 18283 | From subclone of BAC identified with Satt245 | | 53.558 |
| Satt245 | | | | | 53.558 |

S01256 is available through: Genome Systems, Inc. 4633 World Parkway Circle St. Louis, Mo. The sequence of S01256 and equivalent markers is taken from the 3' end of the following sequence

[SEQ ID NO: 105]
TATCATTATA TTGCAGGCTA CNNAAATTTC CAGTNNTAAT

ACAGTATAAT TAAGCAGAGT GTGGTATCTA CAAAATCTCA

ATCCAAACAC ATAATTACAA AACTCTAGAA CAGCAGAACA

CATATAGCAT TTGATTTGAA GTATTCATTC ACTAATTGAT

TAGCCTTAGA AATTCAAATG ATATAATCTG ACCACTCAGA

GATAAAGGAA GTATGGTCCA TGGACTCCCC AGGAACATCC

TCGTGCTTAG AGGGCTTCTC CTTCCCACCA ACCAACCTGG

CTGGGTTCCC AACAGCTGTT GTCTGTGGTG GCACATCGAT

TAAAACCACC GAGCCAGCAC AACCTTTGC ACCTTCCCCG

ATCTTAATAT TCCCCAGAAT GGTAGCACCG GCACCAATAA

GCACCCCATC CCCAATCTTG GGATGCCGGT CCCCACCAAC

TTGCCAGTC CCACCCAGCG TAACGTGGTG CAGGATCGAC

ACATTGTTCC GATCACTGC CGTCTCCCCC ACCACCACCC

CGGTGGCATG GTCGAACAGA TCCCCTTCC CGATCCTCGC

CGCAGGGTGA ATGTCCACCG CGAACACATC GCGATGCGA

GAGTGCAGTG CNAAAGCCAA TGGCTGCCGC GATTGNCGNC

CAACAGATG CGCCACACGG TGCGCCTGCA AAATCACAAT

CACACACAAC TAATCCTAAG ATTCAATAAT CAAAAAGAG

TNNACTNNNC ATACACTGTC ATCNCNNNTA TAGTCATGTT

TCATNNNAAT CTNGNNNNAC AATGCATATA AATTAAACTC AAT

S02020 is available through: Genome Systems, Inc. 4633 World Parkway Circle St. Louis, Mo. The sequence of S02020 and equivalent markers is taken from the 3' end of the following sequence:

[SEQ ID NO: 106]
AAAGNNAACA TTTTTGTTTA TATGACNNNA ACAAACTGCA

AAGAAAAATT GTTAAAAACC AGAAGCAATT TAGGTGATCA

CAAATACCAC ATGCTTACAC CTTCCAGTGA CAAGTACAGT

ATGTTGTGGC ACCAGCCGTT TCAGTTGATG CAAACTTGCT

TCGTGCCAAA ATTCTAACAA CACAACTACC TAAGCTATCA

AACAAGAGAA GCCCTTTTGT CCTTTGGTCG ACCTATCAAA

GGTCATCAGA TCACACTAGT CCTACCCTTT TAAGAAAACC

TACTATCAAC AGTCATATGT ATCTCATGAA AAGCACATAA

AAACATGTCA CTTTGCCTCT TCACCATCTC CACTGTTATG

AGCAGCCGCG GAGCTGCCTT GGCCGTCTCC ACCAGCTGTT

CCAGCCTCAG AGGCATCTTG CTTGCTTCCA CCACGTGCAT

CGTTTGGACC AGTAGCCGAA GGTGGACCAC CGCTGTTTCC

CCTCCAAGAG CAGCCTCACT GTGCATTGGA TGCATGCCA

TTATTTATAT CTCCAGGTCT AAGTCCCATT TGACCTTGGA

TGGCCTGCTG GTGTAGCTGC TGTTGTTGTT CCTGCATTTG

ATGTGGATTG CCAAATTGCA ATGGCATTTT CTGGGGGAAC

ANNCCTTGCT GCTGCTGNNN NATTGCTGCT GCAGCNNNNT

GNNNATNNNN NATATANNNN NC

S04309 is available through: Genome Systems, Inc. 4633 World Parkway Circle St. Louis, Mo. The sequence of S04309 and equivalent markers is taken from the 3' end of the following sequence:

[SEQ ID NO: 107]
TATCATTATA TTGCAGGCTA CNNAAATTTC CAGTNNTAAT

ACAGTATAAT TAAGCAGAGT GTGGTATCTA CAAAATCTCA

ATCCAAACAC ATAATTACAA AACTCTAGAA CAGCAGAACA

```
                                            -continued
CATATAGCAT TTGATTTGAA GTATTCATTC ACTAATTGAT

TAGCCTTAGA AATTCAAATG ATATAATCTG ACCACTCAGA

GATAAAGGAA GTATGGTCCA TGGACTCCCC AGGAACATCC

TCGTGCTTAG AGGGCTTCTC CTTCCCACCA ACCAACCTGG

CTGGGTTCCC AACAGCTGTT GTCTGTGGTG GCACATCGAT

TAAAACCACC GAGCCAGCAC CAACCTTTGC ACCTTCCCCG

ATCTTAATAT TCCCCAGAAT GGTAGCACCG GCACCAATAA

GCACCCCATC CCCAATCTTG GGATGCCGGT CCCCACCAAC

CTTGCCAGTC CACCCAGCG TAACGTGGTG CAGGATCGAC

ACATTGTTCC CGATCACTGC CGTCTCCCCC ACCACCACCC

CGGTGGCATG GTCGAACAGA ATCCCCTTCC GATCCTCGC

CGCAGGGTGA ATGTCCACCG CGAACACATC AGCGATGCGA

AGTGCAGTG CNAAAGCCAA TGGCTGCCGC GATTGNCGNC

ACAACAGATG GCCACACGG TGCGCCTGCA AAATCACAAT

CACACACAAC TAATCCTAAG ATTCAATAAT CAAAAAAGAG

TNNACTNNNC ATACACTGTC ATCNCNNNTA TAGTCATGTT

TCATNNNAAT CTNGNNNNAC AATGCATATA AATTAAACTC AAT
```

S01623 is available through: Genome Systems, Inc. 4633 World Parkway Circle St. Louis, Mo. The sequence of S01623 and equivalent markers is taken from the 3' end of the following sequence:

```
                                              [SEQ ID NO: 108]
AAGACANNNN CGTTACATAA TCCTCACATA TAGTCATCCA

ATCAGAACTG AATAGGAAAA AAAAATACAC AATATTAATG

AAATTTAATT TATCATCTGC ATGTTTGGAT AAGCGTCAAA

GGTAAACCTA CTATTAGTAG CTTTCTTGTC TTTCCTTCAA

TTTGACGTGA TTTTAGTTTG AGACGTGCAT GTATAAAGTG

GATCCAAACA CACTATTATG GTATGCAGAG TGAAGTAAAA

ACTTAAAAAT CAGAGCAGCG ACCATTGCGT TCCCAGTCAC

CATACCTAGT GGGCTCAGGC CCTTGGGTC CACCAATCTC

ACCTGTTTCT TTGTTAATAC TGTCACCATC TTCGTGGTCT

TCTTCGGGCT CATGGCTTTG TTTGTTCTCA TCATGGAGAG

ATTCTTGAGG TGGTGTCTGT GCTTGTTCCC TGAGNGGGTT

TTCGTGTTGT GGCTGAGTTG AAGAGCAGNN GAGCCGTGTC

ACTGTGTTGG AAACAAAATG GTAAACTGC TCGGATTTGG

TGCGGTGANN NNCNNTGTTG GCTACACAAG CAGTGAGCG

AGGGAANNNG GTGGTCATTG TTGTTTGTTA ATGATGTAAG

GCAGATGATC AGAAANNAGA AAACTCGTAN CNNNACGAAC

AAAACCCTGA AATGGTTTAA AGCTNNNCCT TGGATTTTGA

TTCTTGTTGC TGCGCGTTNG NNTGC
```

Markers that map closer to the RAG locus are preferred over markers that map farther from the RAG locus for use in this invention. A more preferred set of markers includes: Satt150, Sat_316, A351_1, Mng339_1, Ts, S01256, S02020, Satt567, Satt540, Bng222_1, RGA_2b, RGA5b, GM260, S04309, Satt435, R079_1, A060-2, DOP_H14, GM260, A131_1, Sat_244, S01623, Satt463, Sat_253, S03544, Satt245, GM284, A946_2, GM256, GMS057, Satt220, A584_3, Satt626, OP_N04, Satt323, Sat_258, Satt702, L204_4, GMS003b, Satt536, Sat_003, OM11_1100, Sat_148, Bng179_2, K417_3, Sat_226, Satt175, K024_1, A226_1, GM230, ACCAGC315, Satt494, B157_2, A715_1, and Sct_147.

A most preferred set of markers from which to choose at least one marker for use in this invention includes Satt435, Satt463, Satt245, S04309, S01623, and DOP_H14.

The markers may be any type of mapped molecular marker or phenotypic trait known to the art, including restriction fragment length polymorphism (RFLP) markers, target region amplification polymorphism (TRAP) markers, random amplified polymorphic (RAPD) markers, single sequence repeat (SSR) markers, single nucleotide polymorphism (SNP) markers, and isozyme markers.

In one embodiment of the invention, markers flanking the RAG locus are used in the marker-assisted selection processes of this invention. The genomic DNA of soybean germplasm is preferably tested for the presence of at least two of the foregoing molecular markers, one on each side of the RAG locus. Most preferably, the two markers are Satt435 and Satt463. Markers that map close to Satt435 and Satt463 can also be used, provided they fall to either side of the RAG locus. Preferably, one of said at least two molecular markers is within at least about 10 to about 20 cM of Satt435 and another of said at least two molecular markers is within at least about 10 to about 20 cM of Satt463, and to ensure that the markers used flank the RAG locus, one of said at least two molecular markers within at least about 10 to about 20 cM of Satt435 should be farther than that distance from Satt463, and another of said at least two molecular markers within at least about 10 to about 20 cM of Satt463 should be farther than that distance from Satt435.

The method of this invention for reliably and predictably introgressing soybean *Aphis glycines* resistance into non-resistant soybean germplasm or less resistant soybean germplasm comprises: providing a first soybean germplasm that has RAG-gene-derived resistance to *Aphis glycines*; providing a second soybean germplasm that lacks RAG-gene-derived resistance to *Aphis glycines*; crossing the first soybean germplasm with the second soybean germplasm to provide progeny soybean germplasm; screening said progeny germplasm to determine the presence of RAG-gene-derived resistance to *Aphis glycines*; and selecting progeny that tests positive for the presence of RAG-gene-derived resistance to *Aphis glycines* as being soybean germplasm into which germplasm having RAG-gene-derived resistance to *Aphis glycines* has been introgressed.

Preferably, the screening and selection are performed by using marker-assisted selection using a marker on major linkage group M as described above.

The screening and selection may also be performed by exposing plants containing said progeny germplasm to aphids of the species *Aphis glycines* in a live aphid assay and selecting those plants showing resistance to aphids as containing soybean germplasm into which germplasm having RAG-gene-derived resistance to *Aphis glycines* has been introgressed. The live aphid assay may be any such assay known to the art, e.g., as described in Hill, C. B., et al., "Resistance to the soybean aphid in soybean germplasm" (2004) Crop Science 44:98-106, Hill, C. B., et al., "Resistance of Glycine species and various cultivated legumes to the soybean aphid (Homoptera: Aphididae)" (2004) J. Economic Entomology 97(3)1071-1077, or "Li, Y. et al., "Effect of three resistant soybean genotypes on the fecundity, mortality, and maturation of soybean aphid (Homoptera: Aphididae)" (2004) J. Economic Entomology 97(3):1106-1111, or as described in the Examples hereof. A preferred method includes placing aphid-infested plant parts on vegetative cotyledon (VC) stage plants and rating aphid population and plant damage weekly. As described herein, a 0-5 rating scale in which 0=no aphids present, 1=a few solitary and transient aphids present, 2=small scattered colonies, 3=dense colonies, 4=dense colonies with plant damage, and 5=dense colonies with severe plant damage, may be used.

The screening and selection may also be done directly by hybridizing nucleic acid from plants containing progeny germplasm to a nucleic acid fragment comprising a RAG gene, and selecting those plants having germplasm that hybridizes to the nucleic acid fragment as having RAG-gene-derived resistance to *Aphis glycines*.

The method of this invention for breeding a soybean plant homozygous for an *Aphis glycines* resistance gene that is a cultivar adapted for conferring, in hybrid combination with a suitable second inbred, resistance to *Aphis glycines*, comprises selecting a first donor parental line possessing the desired *Aphis glycines* resistance, said first donor parental line comprising an *Aphis glycines* resistance gene that is located on major linkage group M; crossing the first donor parental line with a second parental line that is high yielding in hybrid combination to produce a segregating plant population of genetically heterogenous plants; screening the plants of the segregating plant population for the gene; selecting plants from the population having the gene; and breeding by self-crossing the plants containing the gene until a line is obtained that is homozygous for the locus containing the gene and adapted for conferring, in hybrid combination with a suitable second inbred, resistance to *Aphis glycines*.

The screening and selection are preferably performed by using marker-assisted selection as described above, but may also be performed by live aphid bioassay as described above, selecting those plants showing resistance to aphids as containing soybean germplasm having a RAG gene. The screening and selection may also be done by hybridizing nucleic acid from plants containing said progeny germplasm to a nucleic acid fragment comprising a RAG gene and selecting those plants whose germplasm hybridizes to the nucleic acid fragment as having the gene.

As the parental line having soybean aphid resistance, any line known to the art or disclosed herein, as described above, may be used.

Also included in this invention are soybean plants produced by any of the foregoing methods:

Isolated nucleic acid fragments comprising a nucleic acid sequence coding for soybean resistance to *Aphis glycines*, are also included in this invention. The nucleic acid fragment comprises at least a portion of nucleic acid belonging to linkage group M, and further comprises nucleotide sequences falling between molecular markers Satt435 and Satt463. It is capable of hybridizing under stringent conditions to nucleic acid of a soybean cultivar resistant to *Aphis glycines*.

Vectors comprising such nucleic acid fragments, expression products of such vectors expressed in a host compatible therewith, antibodies to the expression product (both polyclonal and monoclonal), and antisense nucleic acid to the nucleic acid fragment are also included within this invention.

This invention also includes soybean plants having resistance to *Aphis glycines* comprising a RAG gene and produced by introgression of DNA containing the gene into a soybean germplasm lacking the gene in its genome, and progeny of said soybean plant.

Seed of a soybean germplasm produced by crossing a soybean variety having *Aphis glycines* resistance in its genome with a soybean variety lacking the RAG gene in its genome, and progeny thereof, is also included in this invention. Such seed, from BC3 or BC4 generations derived from crosses with aphid resistant Dowling×Loda $F_2$ plants using as recurrent parents other soybean lines adapted to Illinois, is also included in this invention.

EXAMPLES

Example 1

Genetic Analysis Identifying the Aphid Resistance Gene in Dowling

Crosses were made between the ancestral soybean cultivar Dowling and two susceptible cultivars, Loda and Williams 82. The parents, $F_1$, and $F_2$ plants were tested in a choice test in the greenhouse using the methods described in Hill, C. B., et al., "Resistance to the soybean aphid in soybean germplasm" (2004) Crop Science 44:98-106. Three weeks after infestation, aphid colonization was visually rated using the following scale: 0=no aphids present, 1=few solitary and transient aphids present, 2=small scattered non-established colonies, 3=dense colonies, and 4=dense colonies with plant damage. Plants were considered resistant with a rating of 0, 1, or 2 and susceptible with a rating of 3 or 4. $F_1$ plants were all resistant to the soybean aphid, indicating that resistance was dominant over susceptibility. $\chi^2$ analyses on the segregation of resistance phenotypes of $F_2$ plants from different $F_1$ plants (families) indicated that a single dominant gene, called Rag1 pending approval by the Soybean Genetics Committee, conditioned resistance (Tables 5and 6). Evaluation of the segregation of aphid resistance in $F_{2:3}$ families confirmed the monogenic dominant inheritance of resistance from Dowling (Table 8).

TABLE 5

REACTIONS OF DOWLING × LODA $F_2$ PLANTS AND PARENTS 21 DAYS AFTER INFESTATION BY THE SOYBEAN APHID

| Family | Number of plants | Observed | | Expected (3:1) | | | |
|---|---|---|---|---|---|---|---|
| | | R[1] | S | R | S | $\chi^2$ | P |
| 4021 | 19 | 14 | 5 | 14.25 | 4.75 | 0.018 | 0.89 |
| 4281 | 14 | 11 | 3 | 10.5 | 3.5 | 0.095 | 0.76 |
| 4301 | 16 | 13 | 3 | 12 | 4 | 0.333 | 0.56 |
| 4302 | 11 | 11 | 0 | 8.25 | 2.75 | 3.667 | 0.06 |
| 4303 | 11 | 9 | 2 | 8.25 | 2.75 | 0.273 | 0.6 |
| 4304 | 12 | 8 | 4 | 9 | 3 | 0.444 | 0.5 |
| 4306 | 15 | 8 | 7 | 11.25 | 3.75 | 3.756 | 0.05 |
| 4307 | 8 | 5 | 3 | 6 | 2 | 0.667 | 0.41 |
| 4308 | 6 | 2 | 4 | 4.5 | 1.5 | 5.556 | 0.02 |
| 4309 | 13 | 9 | 4 | 9.75 | 3.25 | 0.231 | 0.63 |
| 4310 | 10 | 8 | 2 | 7.5 | 2.5 | 0.133 | 0.72 |
| 4343 | 8 | 8 | 0 | 6 | 2 | 2.667 | 0.1 |
| 4344 | 15 | 11 | 4 | 11.25 | 3.75 | 0.022 | 0.88 |
| 4531 | 19 | 15 | 4 | 14.25 | 4.75 | 0.158 | 0.69 |
| Totals | | | | | | 18.023 | 0.32 |
| Pooled | 177 | 132 | 45 | 132.75 | 44.25 | 0.017 | 0.9 |
| Heterogeneity | | | | | | 18.006 | 0.26 |
| Dowling | 32 | 32 | 0 | | | | |
| Loda | 32 | 12 | 31 | | | | |

[1]R (resistant) = 0, 1, 2 aphid colonization rating;
S (susceptible) = 3, 4 rating.
[2]One Loda plant had an aphid colonization rating of 2.

TABLE 6

REACTIONS OF DOWLING × WILLIAMS 82 $F_2$ PLANTS AND PARENTS 21 DAYS AFTER INFESTATION BY THE SOYBEAN APHID

| Population | Number of plants | Observed R[1] | Observed S | Expected (3:1) R | Expected (3:1) S | $\chi^2$ | P |
|---|---|---|---|---|---|---|---|
| 4041 | 179 | 135 | 44 | 134.25 | 44.75 | 0.002 | 0.89 |
| Dowling | 19 | 19 | 0 | | | | |
| Williams 82 | 20 | 0 | 20 | | | | |

[1] R (resistant) = 0, 1, 2 aphid colonization rating;
S (susceptible) = 3, 4 rating.

Example 2

Genetic Analysis Identifying the Resistance Gene in Jackson

Crosses were made between the ancestral soybean cultivar Jackson and Loda. The parents, $F_1$, and $F_2$ plants were tested in a choice test in the greenhouse using the methods described in Hill, C. B., et al., "Resistance to the soybean aphid in soybean germplasm" (2004) Crop Science 44:98-106. Three weeks after infestation, aphid colonization was visually rated using the following scale: 0=no aphids present, 1=few solitary and transient aphids present, 2=small scattered colonies, 3=dense colonies, and 4=dense colonies with plant damage. Plants were considered resistant with a rating of 0, 1, or 2 and susceptible with a rating of 3 or 4. $F_1$ plants were all resistant to the soybean aphid, indicating that resistance was dominant over susceptibility. $\chi^2$ analyses on the segregation of resistance phenotypes of $F_2$ plants from different $F_1$ plants (families) indicated that a single dominant gene (Table 7) was present. Evaluation of the segregation of aphid resistance in $F_{2:3}$ families indicated that the segregation of families did not fit a monogenic dominant inheritance model (Table 8). The unexpected $F_{2:3}$ family segregation ratio may have been due to differential seed production between resistant and susceptible $F_2$ plants. Progeny of $F_2$ plants that produced at least 12 seeds were evaluated so that number plants tested exceeded the minimum required (10 plants) to have high confidence (95%) in detecting double recessive susceptible plants in segregating families with a monogenic dominant gene model. About 80% of the resistant $F_2$ plants produced at least 12 seeds, whereas about 17% of the susceptible $F_2$ plants produced 12 seeds or more.

TABLE 7

REACTIONS OF JACKSON × LODA $F_2$ PLANTS AND PARENTS 21 DAYS AFTER INFESTATION BY THE SOYBEAN APHID.

| Family | Number of plants | Observed R | Observed S | Expected (3:1) R | Expected (3:1) S | $\chi^2$ | P |
|---|---|---|---|---|---|---|---|
| 4123 | 38 | 28 | 10 | 28.5 | 9.5 | 0.04 | 0.85 |
| 4124 | 40 | 28 | 12 | 30 | 10 | 0.53 | 0.47 |
| 4201 | 39 | 29 | 10 | 29.25 | 9.75 | 0.01 | 0.93 |
| 4202 | 38 | 30 | 8 | 28.5 | 9.5 | 0.32 | 0.57 |
| 4203 | 40 | 29 | 11 | 30 | 10 | 0.13 | 0.72 |
| 4204 | 39 | 26 | 13 | 29.25 | 9.75 | 1.44 | 0.23 |
| 4211 | 30 | 21 | 9 | 22.5 | 7.5 | 0.4 | 0.53 |
| 4212 | 40 | 38 | 2 | 30 | 10 | 8.53 | 0 |
| 4213 | 40 | 25 | 15 | 30 | 10 | 3.33 | 0.07 |
| 4214 | 40 | 28 | 12 | 30 | 10 | 0.53 | 0.47 |
| 4215 | 40 | 25 | 15 | 30 | 10 | 3.33 | 0.07 |
| 4216 | 40 | 28 | 12 | 30 | 10 | 0.53 | 0.47 |
| 4432 | 19 | 9 | 10 | 14.25 | 4.75 | 7.74 | 0.01 |
| Totals | | | | | | 26.87 | 0.01 |
| Pooled | 483 | 344 | 139 | 362.25 | 120.75 | 3.68 | 0.06 |
| Heterogeneity | | | | | | 23.2 | 0.02 |
| Jackson | 24 | 24 | 0 | | | | |
| Loda | 51 | 0 | 51 | | | | |

[1] R (resistant) = 0, 1, 2 aphid colonization rating;
S (susceptible) = 3, 4 rating

TABLE 8

REACTIONS OF DOWLING × LODA, DOWLING × WILLIAMS 82, AND JACKSON × LODA $F_{2:3}$ FAMILIES AND 21 DAYS AFTER INFESTATION BY THE SOYBEAN APHID

| $F_{2:3}$ population | Number of families[1] | Observed R[2] | Observed H | Observed S | Expected (1:2:1) R | Expected (1:2:1) H | Expected (1:2:1) S | $\chi^2$ | P |
|---|---|---|---|---|---|---|---|---|---|
| Dowling × Loda | 146 | 31 | 73 | 42 | 36.5 | 73 | 36.5 | 1.65 | 0.44 |
| Dowling × Williams 82 | 128 | 35 | 63 | 30 | 32 | 64 | 32 | 0.42 | 0.81 |
| Jackson × Loda | 206 | 86 | 96 | 24 | 51.5 | 103 | 51.5 | 38.27 | 0 |

[1] 12 seeds of each $F_2$ plant were sown.
[2] R = all plants in an $F_{2:3}$ family were resistant,
H = plants in a family segregated for resistance,
S = all plants in a family were susceptible.

Example 3

Molecular Markers Linked to Rag1

A soybean $F_2$ population developed from a cross between Dowling×Loda was used for mapping the location of Rag1. A total of 90 $F_2$ individuals and the two parents were included in the mapping work. The phenotypic data (aphid colonization on $F_2$ plants) was scored as described above in the genetic analysis.

For genotypic data, DNA was isolated from individual plants and polymerase chain reaction (PCR) was carried out using simple sequence repeat (SSR) markers developed by Dr. Perry Cregan, USDA-ARS (See Table 2). The PCR products were evaluated on gels as previously described in Wang, D.J. et al., "A low-cost, high-throughput polyacrylamide gel electrophoresis system for genotyping with micro satellite DNA markers," (2003) Crop Science 43:1828-1832. Initial screening was done using the parents and two bulked DNA samples to identify polymorphic simple sequence repeat (SSR) markers. Each bulk consisted of pooled DNA samples from five susceptible $F_2$ individuals. A total of about 342 SSR markers were screened against the bulks to identify polymorphic markers potentially associated with aphid resistance. Markers showing strong association with Rag1 were further screened using the entire mapping population to determine linkage relationships and map locations. Joinmap 3.0 was used to create a genetic map. As shown in FIG. 1, Rag1 mapped to Linkage Group M where it is flanked by the SSR markers Satt435 and Satt463 that are 3 cM and 6 cM from the Rag1 locus, respectively.

Example 4

Molecular Markers Linked to Rag1 in Jackson

A soybean $F_2$ population developed from a cross between Jackson and Loda was used for mapping the location of the resistance gene to *Aphis glycines*. A total of 92 $F_2$ individuals and the two parents were included in the mapping work.

The phenotypic data (aphid colonization on $F_2$ plants) was scored as described above in the genetic analysis.

For genotypic data, DNA isolation, PCR, and gel electrophoresis were done as described in Wang, D. J. et al., "A low-cost, high-throughput polyacrylamide gel electrophoresis system for genotyping with micro satellite DNA markers," (2003) Crop Science 43:1828-1832. Three SSR markers, Satt435, Satt463, and Satt245, which are mapped 3 cM, 6 cM, and 13 cM from Rag1 in Dowling (FIG. 2), respectively, showed polymorphism between Jackson and Loda and are associated with aphid resistance in Jackson based on 14 $F_2$ individuals. These three markers were further screened using the entire mapping population to determine linkage relationships and map locations.

Joinmap 3.0 was used to create a genetic map. The *Aphis glycines* resistance gene locus mapped to Linkage Group M where the SSR marker Satt435 is 9 cM away from the gene locus.

Example 5

Location of Rag1 in the Soybean Genetic Map $F_{2:3}$ populations from the cross between Dowling and the two susceptible soybean cultivars, Loda and Williams 82, were used to map Rag1 in Dowling using linked SSR markers Satt150, Satt540, Satt435, Satt463, Satt245, Satt220 and Satt323. See Tables 2 and 3.

One hundred and forty nine $F_2$ plants and their $F_{2:3}$ families from Dowling×Loda were used for initial marker screening and initial mapping of Rag1 in Dowling. One hundred and twenty one $F_{2:3}$ families from Dowling×Williams 82 were used to confirm the Rag1 map location and to construct an integrated map for Rag1 in Dowling.

Figure 2:
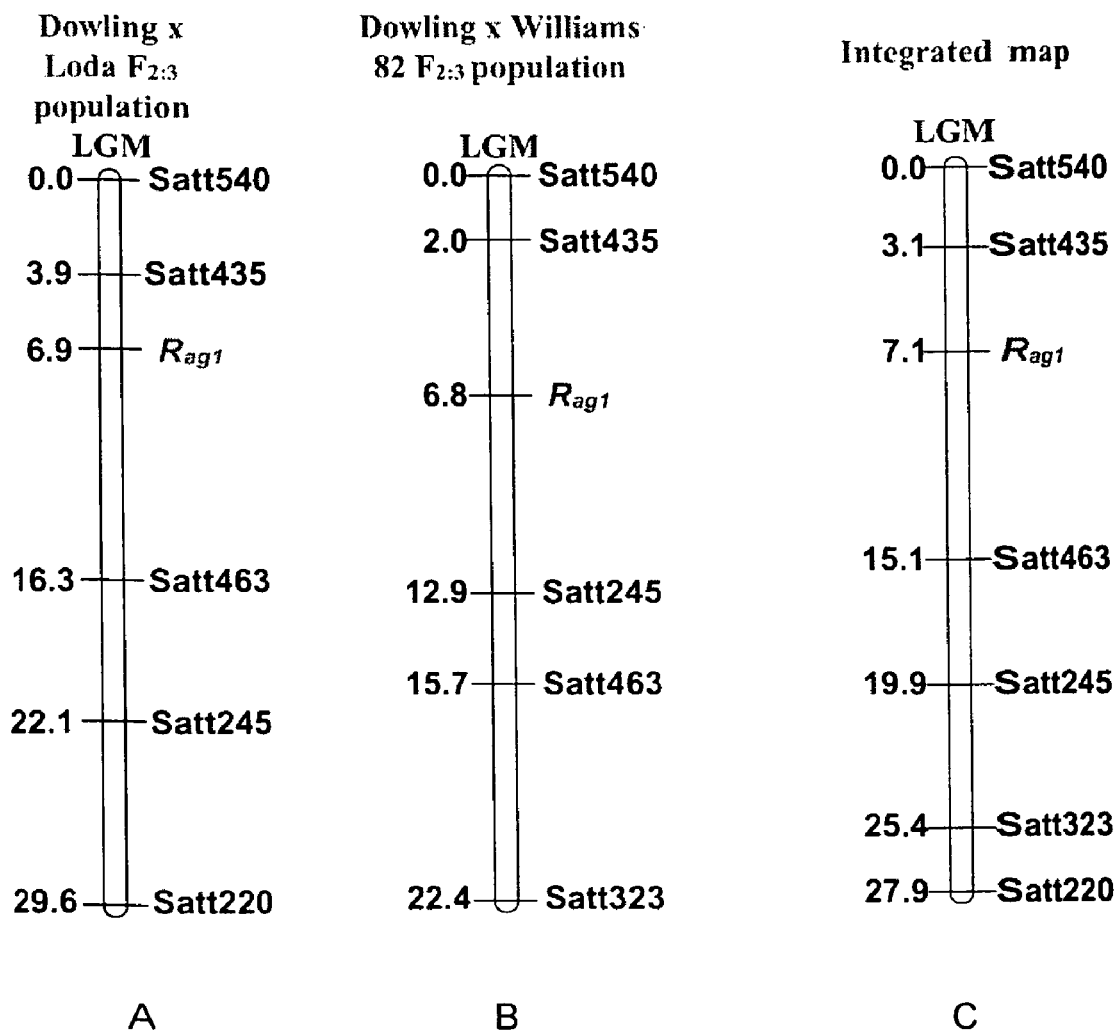
FIG. 2 is a linkage map of soybean linkage group M (LGM) showing the locations of the soybean aphid resistance Rag1 gene A. mapped in a Dowling×Loda mapping population; B. mapped in a Dowling×Williams 82 mapping population; and C. Integrated map from Dowling×Loda and Dowling×Williams 82 mapping populations.
Figure 3:
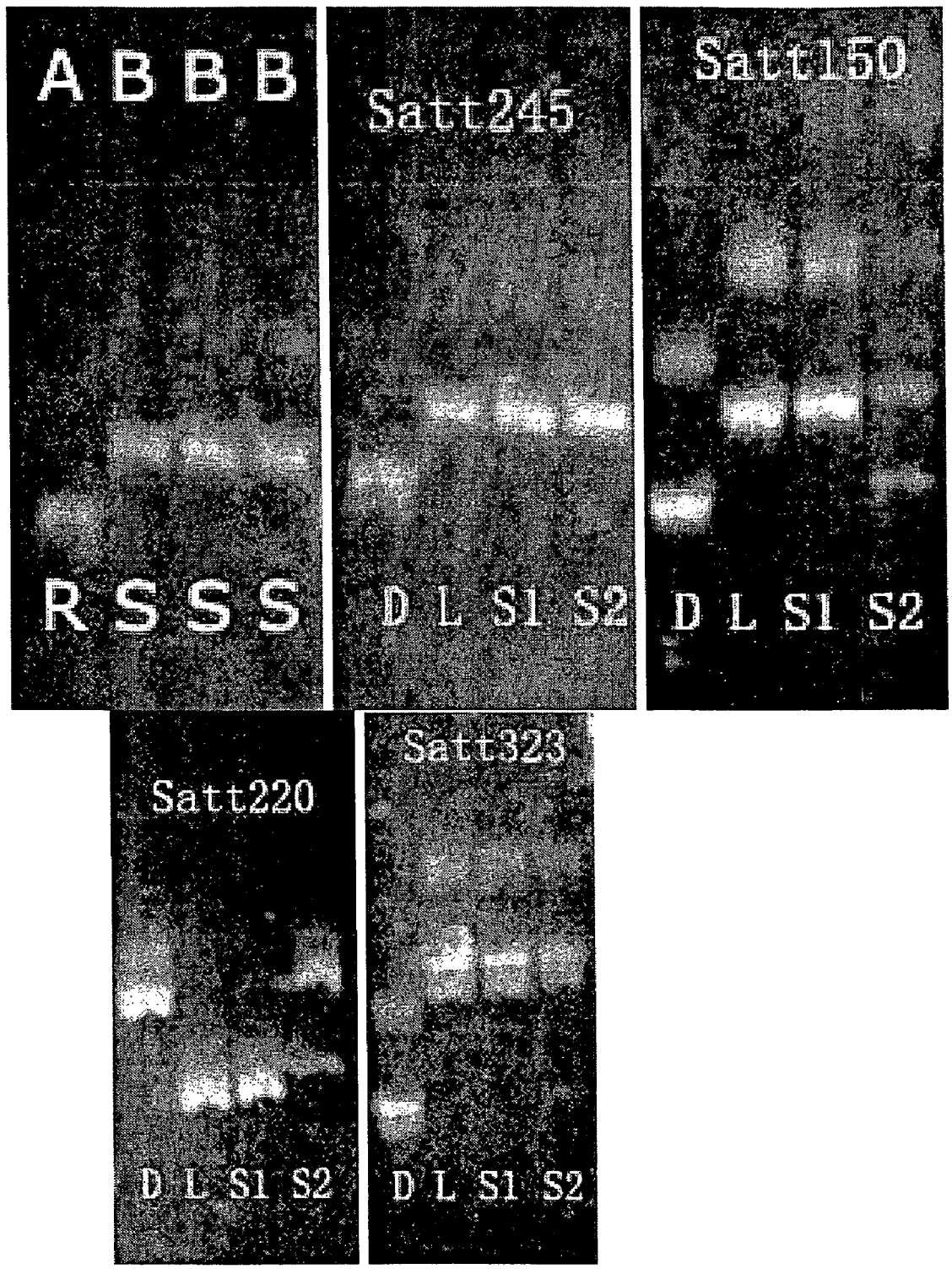
FIG. 3. SSR markers showed co-segregation patterns with Rag1. The ideal PCR amplified band pattern of a co-segregated marker would show A, B, B, B as corresponding to R (resistant parent Dowling, D), S (susceptible parent Loda, L), S (susceptible bulk 1, S1), S (susceptible bulk 2, S2) phenotypes. Among the screened markers, four markers on soybean linkage group M showed potential co-segregation with Rag1. Satt245 showed A, B, B, B pattern, Satt150, Satt220, and Satt323 showed A, B, B, H patterns.

In the integrated map from Dowling×Loda and Dowling×Williams 82 populations, Rag1 was mapped to soybean linkage group M flanked by the SSR markers Satt435 and Satt463 4.0 cM and 8.0 cM from Rag1, respectively (Tables 9 and 10; FIGS. 1 and 2).

Plant Materials

Three $F_{2:3}$ populations from the crosses "Dowling" (PI 548663) ×"Loda" (PI 614088), Dowling ×"Williams 82" (PI 518671) and "Jackson" (PI 548657) ×Loda, and one $F_2$ population of Dowling×Palmetto (PI 548480), were used in this study based on crosses made by Curt Hill. Dowling, Jackson and Palmetto are aphid resistant while Loda and Williams 82 are aphid susceptible. Palmetto was suggested as the origin of the resistance in Jackson because it is the only known resistant ancestor of Jackson (Hill, C. B., et al., "Resistance to the soybean aphid in soybean germplasm" (2004) Crop Science 44:98-106). One hundred and forty nine $F_2$ plants and their $F_{2:3}$ families from Dowling×Loda were used for initial marker screening and initial mapping of Rag1 in Dowling. One hundred and twenty one $F_{2:3}$ families from Dowling×Williams 82 were used to confirm the Rag1 map location and to construct an integrated map for Rag1 in Dowling. One hundred and forty $F_2$ plants and their $F_{2:3}$ families from Jackson×Loda were used to map the gene in Jackson. Sixty-five $F_2$ plants from Dowling×Palmetto were used to test allelism indirectly between Rag1 in Dowling and Jackson. Dowling×Jackson crosses were not made because there are no known polymorphic markers known that could be used to distinguish F1 hybrids from selfs in crosses.

Aphid Clone

The aphid clone was collected from Urbana, Ill. by Dr. Les Domier (USDA-ARS and Department of Crop Sciences, University of Illinois, Urbana, Ill. 61801) and reared on the seedlings of soybean cultivar Williams 82 in a plant growth chamber at 22° C. under continuous 200 μmol m$^{31}$ $^{2}$s$^{-1}$ PAR irradiation.

Soybean Aphid Resistance Phenotyping

The parents, $F_2$ plants, and susceptible checks were screened for aphid resistance under semi-controlled conditions (22-25° C. under continuous 24-h illumination (160-200 μmol m$^{-2}$ s$^{-1}$) in the greenhouse. In a randomized complete block design, seeds were grown in plastic multi-pot inserts within plastic trays without holes. One week later, soybean aphids were transferred from the infested Williams 82 cut stems and leaves to the young test seedlings. Each individual plant was evaluated for aphid score twice at 14 days and 21 days after infestation. Aphid score was rated as index based on aphid population density and plant damage: 0-4, where 0=no aphids observed, 1=few number of aphids scattered on the plant, 2=limited colonization of aphids observed, 3=high aphid density and colonization, 4=high aphid density and colonization plus leaf distortion and plant stunting. After the 21-day rating, insecticide (imidacloprid) was applied. After one week, leaf tissue from the $F_2$ plants was sampled for DNA extraction. All $F_2$ plants were transplanted to 5-inch diameter plastic pots and were grown in the greenhouse under a 12 h photoperiod to produce $F_3$ seeds. In the progeny test, 10-12 $F_3$ seeds per $F_2$ family were evaluated for aphid resistance in a randomized complete block design with three replicates (four $F_3$ plants per $F_2$ family per replicate). $F_2$ genotypes (homozygous resistant, heterozygote, or homozygous susceptible) were inferred from the segregation of the $F_3$ plants.

DNA Isolation, PCR Reaction and Gel Electrophoresis

Young trifoliolate leaves were harvested from the new growth of each individual plant after the aphids were killed. Soybean DNA was extracted from either an individual $F_2$ plant or pooled 10-12 $F_3$ plants, by using either the CTAB method (Keim, P. and Shoemaker, R. C., "Construction of a random recombinant DNA library that is primarily single copy sequence" (1988) Soybean Genet. Newslet. 15:147-148), or DNA quick extraction method (Bell-Johnson, B. et al., "Biotechnology approaches to improving resistance to SCN and SDS: methods for high throughput marker assisted selection" (1998) Soybean Genet. Newslet. 25:115-117).

The PCR amplification was performed in a PTC-220 Thermalcycler manufactured by MJ Research (Waltham, Mass.). PCR reactions were done in 15 μl volumes with 50-250 ng of template DNA, 2 μM primer, 30 mM MgCl$_2$, 3 mM each dNTP, 2.5 unit of Taq polymerase, and 1×PCR buffer. The PCR was performed with an initial denaturing at 94° C. for 4 min, followed by 34 cycles of 25 s of denaturing at 94° C., 25 s of annealing at 47° C., and 25 s of extension at 68° C., with a final 7-min extension at 72° C.

The gel electrophoresis was done using non-denaturing polyacrylamide gels as described before (Wang, D. J. et al., "A low-cost, high-throughput polyacrylamide gel electrophoresis system for genotyping with micro satellite DNA markers," (2003) Crop Science 43:1828-1832). After electrophoresis the gels were photographed and the polymorphic bands were scored as described below.

SSR Marker Screening and Bulk Segregant Analysis

Soybean simple sequence repeat (SSR) markers developed by Dr. Cregan (Cregan, P. B., et al., "An Integrated Genetic Linkage Map of the Soybean Genome" (1999) Crop Science 39:1464-1490) were used in this study. Bulk segregant analysis (Michelmore, R. W., et al., "Identification of markers linked to disease resistance genes by bulked segregant analysis: a rapid method to detect markers in specific genomic regions using segregating populations" (1991) Proc. Natl. Acad. Sci. (USA) 88:9828-9832 in Dowling×Loda $F_2$ population was used to screen for aphid-resistance associated markers. Since at the time of screening, only $F_2$ individuals were available, the resistant $F_2$ plants could be either heterozygous or homozygous, therefore susceptible bulks were used to look for linkage. Two pools of DNA from five susceptible $F_2$ individuals each, bulk A and bulk B were prepared. DNA from resistant parent Dowling and susceptible parent Loda, along with the DNA pools bulk A and B were used to identify polymorphic SSR markers with potential association with aphid resistance. 342 SSR markers were tested for polymorphism between two parents Dowling and Loda, and the segregation patterns for the aphid resistance versus susceptibility. The polymorphic markers with putative linkage with Rag1 were first identified by contrasting bulk segregant analysis, and then were further screened in the whole Dowling×Loda mapping population.

The SSR markers that were determined to map close to Rag1 in the Dowling×Loda mapping population were used to test the polymorphism between Dowling and Williams 82 and between Jackson and Loda. The polymorphic markers were then further screened in the entire population of Dowling×Williams 82 and Jackson×Loda. The data from Dowling×Loda and Dowling×Williams 82 was integrated together to map Rag1 in Dowling, and the data from Jackson×Loda was used to map the gene in Jackson.

The two SSR markers that flanked the Rag1 gene in Dowling and Jackson were found to be monomorphic in Palmetto also, the parent of Jackson.

Genetic mapping

Joinmap 3.0 (Van Ooijen, J. W. and Voorrips, V. E., JoinMap 3.0, Software for the calculation of genetic linkage maps. Plant Research International, Wageningen, the Netherlands (2001)) was used for linkage analysis to create a genetic map using the Kosambi mapping function. A LOD of 3.0 was used as the threshold to group markers into linkage groups. Chi square ($\chi^2$) test at P=0.05 was used to verify the segregation ratio of each locus in the $F_2$ population. The genotypes of the SSR markers were scored as either co-dominant (A=RR, H=Rr, B=rr) or dominant (D=A+H, B or A, C=B+H). Genotypes of the $F_2$ aphid population were scored as co-dominant (A, H, B) after confirmation with the $F_3$ progeny test. Those that had less than 10 $F_3$ seeds available from the $F_2$ plant were scored as dominant (D, B). All of the SSR markers and aphid resistance genes were set to the corresponding $\chi^2$-test classification as described in Joinmap 3.0, 1:2:1 (A: H: B) or 3:1 (A+H+D: B=3:1) segregation ratio.

TABLE 9

$\chi^2$-TEST OF THE SEGREGATION RATIO FOR $R_{AG}1$
AND THE LINKED SSR MARKERS IN THE $F_2$ POPULATION
FROM THE CROSS OF DOWLING × LODA.

| Locus | a | h | b | c | d | — | $\chi^2$ | Classes |
|---|---|---|---|---|---|---|---|---|
| Rag1 | 26 | 72 | 44 | 1 | 5 | 1 | 1.9 | [a + h + d:b] |
| Satt150 | 25 | 61 | 35 | 1 | 8 | 19 | 0.3 | [a + h + d:b] |
| Satt220 | 22 | 24 | 31 | 4 | 33 | 35 | 0.6 | [a + h + d:b] |
| Satt245 | 24 | 76 | 43 | 0 | 3 | 3 | 1.5 | [a + h + d:b] |
| Satt435 | 17 | 68 | 46 | 1 | 13 | 4 | 3.7 | [a + h + d:b] |
| Satt463 | 35 | 57 | 39 | 0 | 11 | 7 | 0.5 | [a + h + d:b] |
| Satt540 | 19 | 81 | 38 | 1 | 6 | 4 | 0.1 | [a + h + d:b] |

TABLE 10

$\chi^2$-TEST OF THE SEGREGATION RATIO FOR RAG1
AND THE LINKED SSR MARKERS IN THE $F_2$ POPULATION
FROM THE CROSS OF DOWLING × WILLIAMS 82

| Locus | a | h | b | c | d | — | $\chi^2$ | Classes |
|---|---|---|---|---|---|---|---|---|
| Rag1 | 25 | 69 | 27 | 0 | 0 | 0 | 2.5 | [a:h:b] |
| Satt150 | 31 | 42 | 25 | 2 | 13 | 8 | 0.4 | [a + h + d:b] |
| Satt245 | 22 | 67 | 22 | 3 | 5 | 2 | 2.3 | [a + h + d:b] |
| Satt323 | 27 | 59 | 28 | 4 | 2 | 1 | 0.1 | [a + h + d:b] |
| Satt435 | 21 | 62 | 27 | 1 | 10 | 0 | 0.4 | [a + h + d:b] |
| Satt463 | 31 | 55 | 22 | 3 | 10 | 0 | 2.5 | [a + h + d:b] |
| Satt540 | 19 | 63 | 25 | 8 | 5 | 1 | 0.4 | [a + h + d:b] |

Example 6

Location of *Aphis Glycines* Resistance Gene in the Soybean Genetic Map

One hundred and forty $F_2$ plants and their $F_{2:3}$ families from Jackson×Loda were used to map the RAG gene in Jackson using linked SSR markers (Tables 2 and 3).

The RAG gene was mapped to linkage group M flanked by markers Satt435 and Satt463 1.9 cM and 7.7 cM, respectively (Table 11; FIGS. 1 and 2).

TABLE 11

χ²-TEST OF THE SEGREGATION RATIO FOR THE RAG GENE AND THE LINKED SSR MARKERS IN THE F₂ POPULATION FROM THE CROSS OF JACKSON × LODA

| Locus   | a  | h  | b  | c  | d  | —  | $\chi^2$ | Classes       |
|---------|----|----|----|----|----|----|----------|---------------|
| RAG     | 40 | 58 | 26 | 0  | 16 | 0  | 3.1      | [a + h + d:b] |
| Satt150 | 29 | 53 | 20 | 4  | 14 | 20 | 3.7      | [a + h + d:b] |
| Satt220 | 46 | 56 | 14 | 10 | 7  | 7  | 12.2*    | [a + h + d:b] |
| Satt245 | 47 | 42 | 24 | 0  | 9  | 18 | 1.9      | [a + h + d:b] |
| Satt435 | 43 | 65 | 26 | 0  | 6  | 0  | 3.1      | [a + h + d:b] |
| Satt463 | 40 | 57 | 32 | 0  | 8  | 3  | 0.2      | [a + h + d:b] |
| Satt540 | 38 | 68 | 24 | 7  | 2  | 1  | 3.3      | [a + h + d:b] |

Although the foregoing invention has been described in detail for purposes of clarity and understanding, it will be clear to those skilled in the art that equivalent cultivars, markers, and methods may be practiced within the scope of the claims hereof.

The invention claimed is:

1. A method for identifying the presence or absence of a gene coding for resistance to *Aphis glycines* in soybean germplasm comprising:
analyzing said germplasm by marker-assisted selection (MAS) to:
detect a resistance to *Aphis glycines* (RAG) locus that maps to soybean linkage group M of said soybean germplasm, wherein said RAG locus is flanked on opposite sides by SSR markers Satt435 and Satt463, which show allelic polymorphism between *Aphis glycines*-resistant and *Aphis glycines*-susceptible soybean genotypes and are linked to the RAG locus, and wherein the RAG locus comprises allelic DNA sequences that control resistance to *Aphis glycines*; and
determine the presence or absence of an allelic form of DNA linked to the gene coding for resistance to *Aphis glycines* in said germplasm;
wherein the presence or absence of said allelic form of DNA linked to said gene is determined by comparing a first PCR-amplified polymorphic marker fragment of said soybean germplasm to a second PCR-amplified polymorphic marker fragment of soybean germplasm from a plant having *Aphis glycines* resistance conferred by said Rap1 gene, wherein said second fragment is made using the same marker used to make said first fragment, and wherein said second fragment has a size substantially the same as that of a PCR-amplified polymorphic marker fragment of germplasm of *Aphis glycines*-resistant soybean varieties Dowling and Jackson made using the same marker used to make said first and second fragments; and
determining that said gene coding for RAG resistance is present in said soybean germplasm when said first fragment is substantially the same size as said second fragment, and determining that said gene is not present in said germplasm when said first fragment is not substantially the same size as said second fragment.

2. The method of claim 1 also comprising hybridizing a nucleic acid fragment, which comprises the sequence of, or a primer sequence of, a DNA marker that maps to within 10 cM of said Satt435 and/or Satt463 SSR markers, to nucleic acid of soybean linkage group M of said soybean germplasm.

3. The method of claim 1 also comprising hybridizing a nucleic acid fragment, or a primer sequence thereof, which comprises a sequence of a DNA marker that maps to within 20 cM of said Satt435 and/or Satt463 SSR markers, to nucleic acid of soybean linkage group M of said soybean germplasm.

4. The method of claim 3 wherein said marker that maps to within 20 cM of said Satt435 and/or Satt463 markers is a DNA marker selected from the group consisting of SSR, RFLP, SNP, and RAPD markers.

5. The method of claim 2 wherein at least two of said DNA marker nucleic acid fragments, that map to within 10 cM of said Satt435 and/or Satt463 SSR markers and that comprise sequences that flank said RAG locus on opposite sides, are hybridized to said nucleic acid of soybean linkage group M of said soybean germplasm.

6. The method of claim 3 wherein at least two of said DNA marker nucleic acid fragments, that map to within 20 cM of said Satt435 and/or Satt463 SSR markers and that have sequences that flank said RAG locus on opposite sides, are hybridized to said nucleic acid of soybean linkage group M of said soybean germplasm.

7. The method of claim 1 wherein said detecting step includes hybridizing at least one polymorphic marker, which is linked to the gene coding for resistance to *Aphis glycines* and maps between about 3 and about 20 cM from Satt435 or Satt463, with nucleic acid of soybean linkage group M of said soybean germplasm.

* * * * *